(12) United States Patent
Prasad et al.

(10) Patent No.: US 11,614,419 B2
(45) Date of Patent: *Mar. 28, 2023

(54) TRI-ELECTRODE APPARATUS AND METHODS FOR MOLECULAR ANALYSIS

(71) Applicant: Board of Regents, The University of Texas System, Austin, TX (US)

(72) Inventors: Shalini Prasad, Allen, TX (US); Anjan Panneer Selvam, Richardson, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 269 days.

This patent is subject to a terminal disclaimer.

(21) Appl. No.: 16/829,650

(22) Filed: Mar. 25, 2020

(65) Prior Publication Data

US 2020/0240939 A1 Jul. 30, 2020

Related U.S. Application Data

(62) Division of application No. 14/640,408, filed on Mar. 6, 2015, now Pat. No. 10,641,721.

(60) Provisional application No. 62/110,141, filed on Jan. 30, 2015, provisional application No. 61/949,858, filed on Mar. 7, 2014.

(51) Int. Cl.
*G01N 27/02* (2006.01)

(52) U.S. Cl.
CPC ......... *G01N 27/028* (2013.01); *G01N 27/026* (2013.01); *Y10T 29/49128* (2015.01)

(58) Field of Classification Search
CPC .................. G01N 27/026; G01N 27/028
See application file for complete search history.

(56) References Cited

U.S. PATENT DOCUMENTS

| | | | |
|---|---|---|---|
| 4,863,757 A | 9/1989 | Durand | |
| 5,494,831 A * | 2/1996 | Kindler | G01N 33/5438 204/422 |
| 5,650,061 A | 7/1997 | Kuhr et al. | |
| 6,114,930 A | 9/2000 | Gobbi et al. | |

(Continued)

FOREIGN PATENT DOCUMENTS

| | | |
|---|---|---|
| AU | 2015227036 | 9/2016 |
| CN | 106164659 | 11/2016 |

(Continued)

OTHER PUBLICATIONS

Bohinc, et al. "Thickness of electrical double layer. Effect of ion size" *Electrochimica Acta*, 2001, 46:3033-3040.

(Continued)

*Primary Examiner* — Alesa Allgood
(74) *Attorney, Agent, or Firm* — Norton Rose Fulbright US LLP

(57) ABSTRACT

The claimed invention is an apparatus and method for performing impedance spectroscopy with a handheld measuring device. Conformal analyte sensor circuits comprising a porous nanotextured substrate and a conductive material situated on the top surface of the solid substrate in a circuit design may be used alone or in combination with a handheld potentiometer. Also disclosed are methods of detecting and/or quantifying target analytes in a sample using a handheld measuring device.

18 Claims, 13 Drawing Sheets

(56) References Cited

U.S. PATENT DOCUMENTS

| | | | | |
|---|---|---|---|---|
| 8,623,660 | B2* | 1/2014 | Kraft | G01N 27/3273 436/95 |
| 10,641,721 | B2 | 5/2020 | Prasad | |
| 2003/0144581 | A1 | 7/2003 | Conn et al. | |
| 2004/0157337 | A1 | 8/2004 | Burke et al. | |
| 2004/0189311 | A1* | 9/2004 | Glezer | G01N 21/76 324/444 |
| 2005/0031139 | A1* | 2/2005 | Browning | H04R 3/002 381/59 |
| 2005/0147877 | A1 | 7/2005 | Tarnowski | |
| 2005/0194250 | A1 | 9/2005 | Frey et al. | |
| 2005/0227373 | A1 | 10/2005 | Flandre et al. | |
| 2008/0179198 | A1 | 7/2008 | Burgess et al. | |
| 2009/0242429 | A1 | 10/2009 | Sitdikov et al. | |
| 2012/0205258 | A1 | 8/2012 | Noble et al. | |
| 2012/0226121 | A1 | 9/2012 | Kamath et al. | |
| 2013/0201316 | A1* | 8/2013 | Binder | H04L 67/12 701/2 |
| 2013/0224765 | A1 | 8/2013 | Prasad et al. | |
| 2013/0332085 | A1* | 12/2013 | Yang | G01N 27/416 702/22 |
| 2014/0084949 | A1* | 3/2014 | Smith | A61B 8/429 324/693 |
| 2020/0240939 | A1 | 7/2020 | Prasad | |

FOREIGN PATENT DOCUMENTS

| | | |
|---|---|---|
| EP | 3114466 | 1/2017 |
| JP | 2017507341 | 3/2017 |
| KR | 20160130459 | 11/2016 |
| WO | WO 2013/030369 | 3/2013 |
| WO | WO 2015/134862 | 9/2015 |

OTHER PUBLICATIONS

Extended European Search Report issued in European Application No. 15758509.2, dated Feb. 2, 2018.

Hang, et al. "Discussion on the position of the shear plane," *Journal of Colloid and Interface Science*, 2003, 258:40-44.

International Search Report and Written Opinion issued in International Patent Application No. PCT/US2015/019158, dated Jun. 17, 2015.

Lisdat, et al. "The use of electrochemical impedance spectroscopy for biosensing," *Analytical and Bioanalytical Chemistry*, 2008, 391.5:1555.

Reighard, et al. "Conformal Coating Process Controls: the Manufacturing Engineer's Aid," *APEX*, 2000.

Santos, et al. "Fundamentals and application of impedimetric and redox capacitive biosensors," *Journal of Analytical and Bioanalytical Techniques*, 2015, S7:1.

Vestergaard, et al. "An overview of label-free electrochemical protein sensors," *Sensors*, 2007, 7(12):3442-3458.

Office Action issued in corresponding Canadian Patent Application No. 2,941,382 dated Dec. 15, 2022.

* cited by examiner

| species | OPTIMAL SYSTEM | Receptor | frequency | Phase | Detection Limits |
|---|---|---|---|---|---|
| protein | 2 or 3 electrode | Antibody | under 1000 Hz | sync | 1 fg/mL |
| long, ds DNA | 3 electrode | ssDNA,dsDNA | under 1000 Hz | sync | 1 mM |
| long RNA | 3 electrode | ssDNA,dsDNA | under 1000 Hz | sync | 1 mM |
| DNA oligo | 3 electrode | ssDNA,dsDNA | under 1000 Hz | sync | 1 mM |
| miRNA | 2 or 3 electrode | miRNA | under 1000 Hz | sync | 10 nM |
| steroids | 2 or 3 electrode | enzyme,antibody | under 1000 Hz | sync | 1 pg/mL |
| fatty acids | 2 or 3 electrode | enzyme,antibody | under 1000 Hz | sync | 1 pg/mL |
| lipids/phospholipids | 2 or 3 electrode | enzyme,antibody | under 1000 Hz | sync | 1 pg/mL |
| LPS | 2 or 3 electrode | Antibody | under 1000 Hz | sync | |

FIG. 13

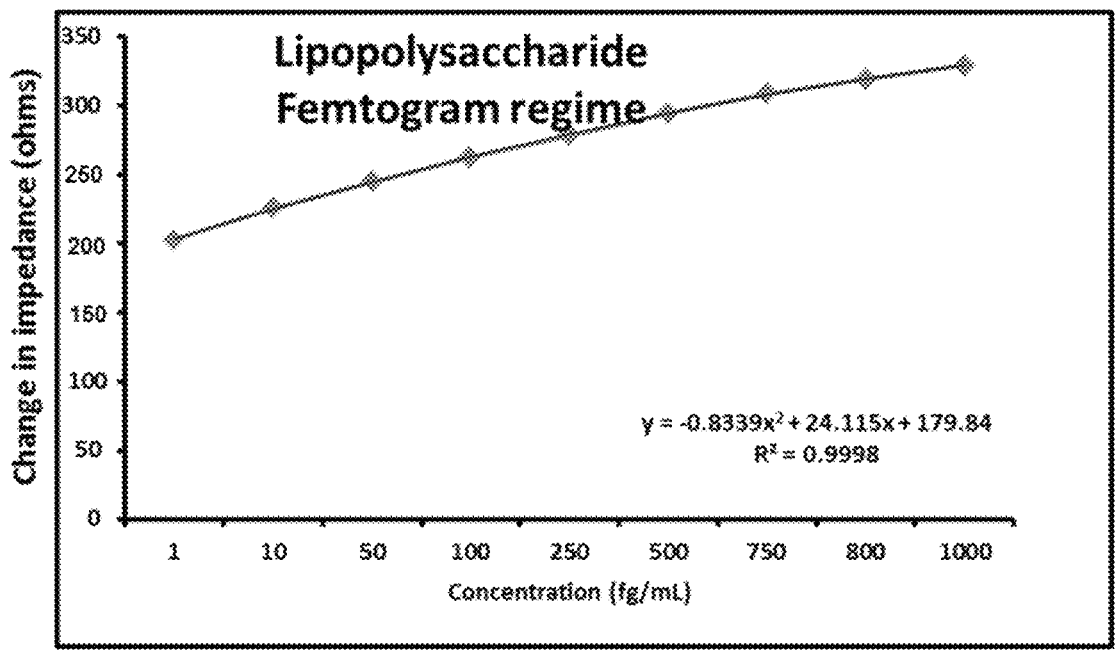

FIG. 14

- Impedance @ capture probe: 32.452 kohms

- Impedance @ capture probe: 32.452 kohms

TRI-ELECTRODE APPARATUS AND METHODS FOR MOLECULAR ANALYSIS

CROSS REFERENCE TO RELATED APPLICATION

This application is a divisional application of U.S. patent application Ser. No. 14/640,408, filed Mar. 6, 2015, which claims the benefit of priority to U.S. Provisional Patent Application Serial Nos. 61/949,858 filed Mar. 7, 2014 and 62/110,141 filed Jan. 30, 2015, the contents of each of which are incorporated herein by reference in their entirety.

BACKGROUND OF THE INVENTION

1. Field of the Invention

The present invention relates generally to the field of detection devices. More particularly, it concerns apparatus and methods utilizing three electrode potentiostats to detect biomolecules and other target analytes in a concurrent manner.

2. Description of Related Art

The ability to design, cheap and disposable diagnostics and analytical platforms that are also biodegradable is of great value to health care as well as the environment. It has been established that size based confinement of biomolecules is critical for achieving enhanced sensitivity in diagnostics. Typically, size based confinement is achieved through complex fabrication processes as used for complementary metal-oxide-semiconductor (CMOS) technologies, which increases the cost per unit and increases the effective cost of the technology. Low cost technologies use printed circuit boards which are difficult to dispose and add costs to the environment due to poor biodegradability. Paper-based microfluidics have been developed that typically use screen printing technologies; however, issues remain with respect to achieving controlled fluid flow on top the surfaces.

Similarly, currently available market potentiostats are designed with the focus of applicability to a wide range of electrical/electrochemical techniques. This leads to bulky form factors and expensive components used in their construction. Moreover, they are designed to be used for electrochemical applications. Specific problems with such market potentiostats include the fact that they have large device form factors, making it difficult for use in point-of-care settings, have high noise at low current and low voltage settings, have expensive and repetitive software and firmware costs, have analog serial input/output interfaces, and have low robustness and non-universality in global application. On the other extreme, handheld portable potentiostats are very limited in customizability and applicability to a range of applications. Portable potentiostats are not noise efficient for biological applications and hence lack robustness. Specific problems with handheld potentiostats include high noise at low current and low voltage settings, low robustness for application to biosensing, and minimal operation choices for electrochemical applications.

Currently available market potentiostats are available as two electrode and three electrode systems. Both the currently available two electrode and three electrode potentiostats apply a single input voltage between two electrodes. This single applied input voltage suffers from limited specificity in detecting target analytes.

Therefore, there remains a need for affordable, efficient, biodegradable diagnostic platforms having enhanced specificity in detecting target analytes.

SUMMARY OF THE INVENTION

Exemplary embodiments of the claimed invention include apparatus and methods for performing impedance spectroscopy with a handheld potentiometer.

Exemplary embodiments include a method of detecting or quantifying multiple target analytes in a sample using a handheld measuring device and a conformal analyte sensor circuit comprising the steps of: (a) placing a sample containing multiple target analytes on a conformal substrate having a sensor circuit comprising a first electrode, a second electrode, and a third electrode; (b) applying a first alternating input electric voltage between the first electrode and the second electrode at a first phase angle; (c) applying a second alternating input electric voltage between the third electrode and the second electrode at a second phase angle, wherein the first phase angle and the second phase angle are separated by a constant delta phase angle; (d) measuring the output current at different frequencies and varying phase angles for different analytes; (e) amplifying an output current flowing from the first electrode and from the third electrode through the second electrode using a programmable gain amplifier; (f) sectioning an electrical double layer into a plurality of planes, wherein the electrical double layer is proximal to a surface of first electrode, a surface of the second electrode, and a surface of the third electrode; (g) varying the first phase angle of the first input electric voltage and the second phase angle of the second input electric voltage; (h) identifying the first phase angle and the second phase angle at which a maximum impedance change occurs; (i) measuring the impedance identified at the first phase angle and the second phase angle; and (j) using the measured impedance and associated phase angle at different frequencies to detect multiple target analytes or calculate concentrations of target analytes by use of a standard calibration curve.

Particular embodiments include an analyte sensor circuit comprising: a substrate having a surface comprising a conductive material (with or without textured porosity) situated on the surface in a circuit design, thereby creating a circuit comprising a first electrode, a second electrode and a third electrode; a programmable gain amplifier operably coupled to the first electrode, the second electrode, and the third electrode; and a programmable microcontroller operably coupled to the programmable gain amplifier, the first electrode, the second electrode, and the third electrode, wherein the programmable microcontroller is configured to: (a) apply a first alternating input electric voltage between the first electrode and the second electrode of the conformal analyte sensor circuit; (b) apply a second alternating input electric voltage between the third electrode and the second electrode at a second phase angle, wherein the first phase angle and the second phase angle are separated by a constant delta phase angle; (c) amplify an output current flowing from the first electrode and from the third electrode through the second electrode using a programmable gain amplifier; (d) section an electrical double layer into a plurality of planes in three dimensional space, wherein the electrical double layer is proximal to a surface of the first electrode, a surface of the second electrode and to a surface of the third electrode; (e) vary the first phase angle of the first input electric voltage and the second phase angle of the second input electric voltage; (f) identify the first phase angle and the second phase angle at which a maximum impedance change occurs; (g) measure the impedance identified at the first phase angle and the second phase angle; and (i) use the measured impedance to detect the target analyte or calculate a concentration of the target analyte by use of a standard calibration curve.

In certain embodiments, the device comprises additional circuits and each circuit comprises a first electrode, a second electrode and a third electrode each operably coupled to the programmable gain amplifier. In particular embodiments, the programmable microcontroller is configured to perform steps (a)-(i) for each of the additional circuits.

Exemplary embodiments include a device configured to detect and quantify analytes, the device comprising: a conformal sensor circuit; and a handheld reader coupled to the conformal sensor circuit, wherein the device is configured simultaneously detect and quantify multiple target analytes from a single sample.

In certain embodiments, the conformal sensor circuit comprises: a substrate having a surface comprising a conductive material situated on the surface in a circuit design, thereby creating a circuit comprising a first electrode, a second electrode and a third electrode; a programmable gain amplifier operably coupled to the first electrode, the second electrode, and the third electrode; and a programmable microcontroller operably coupled to the programmable gain amplifier, the first electrode, the second electrode, and the third electrode, wherein the programmable microcontroller is configured to: (a) apply a first alternating input electric voltage between the first electrode and the second electrode of the conformal analyte sensor circuit; (b) apply a second alternating input electric voltage between the third electrode and the second electrode at a second phase angle, wherein the first phase angle and the second phase angle are separated by a constant delta phase angle; (c) amplify an output current flowing from the first electrode and from the third electrode through the second electrode using a programmable gain amplifier; (d) section an electrical double layer into a plurality of planes in three dimensional space, wherein the electrical double layer is proximal to a surface of the first electrode, a surface of the second electrode and to a surface of the third electrode; (e) vary the first phase angle of the first input electric voltage and the second phase angle of the second input electric voltage; (f) identify the first phase angle and the second phase angle at which a maximum impedance change occurs; (g) measure the impedance identified at the first phase angle and the second phase angle; and (i) use the measured impedance to detect the target analyte or calculate a concentration of the target analyte by use of a standard calibration curve.

Exemplary embodiments include a method of detecting or quantifying a target analyte in a sample using a handheld measuring device and a conformal analyte sensor circuit comprising the steps of: (a) placing a sample containing multiple target analytes on a conformal substrate having a sensor circuit comprising a first electrode, a second electrode, a third electrode, a fourth electrode, a fifth electrode and a sixth electrode; (b) applying a first alternating input electric voltage between the first electrode and the second electrode at a first phase angle; (c) applying a second alternating input electric voltage between the third electrode and the second electrode at a second phase angle, wherein the first phase angle and the second phase angle are separated by a first constant delta phase angle; (d) measuring a first output current at different frequencies over a first range of frequencies and varying phase angles over a first range of phase angles; (e) amplifying the first output current flowing from the first electrode and from the third electrode through the second electrode using a programmable gain amplifier; (f) sectioning a first electrical double layer into a plurality of planes in three dimensional space, wherein the first electrical double layer is proximal to a surface of first electrode, a surface of the second electrode, and a surface of the third electrode; (g) varying the first phase angle of the first input electric voltage and the second phase angle of the second input electric voltage over the first range of phase angles; (h) identifying the first phase angle and the second phase angle at which a first maximum impedance change occurs; (i) measuring the impedance identified at the first phase angle and the second phase angle; (j) using the measured impedance at different frequencies to detect a first target analyte or calculate a concentration of the first target analyte by use of a standard calibration curve; (k) applying a third alternating input electric voltage between the fourth electrode and the fifth electrode at a third phase angle; (l) applying a fourth alternating input electric voltage between the sixth electrode and the fifth electrode at a fourth phase angle, wherein the third phase angle and the fourth phase angle are separated by a second constant delta phase angle; (m) measuring a second output current at different frequencies over a second range of frequencies and varying phase angles over a second range of phase angles; (n) amplifying the second output current flowing from the fourth electrode and from the sixth electrode through the fifth electrode using the programmable gain amplifier; (o) sectioning a second electrical double layer into a plurality of planes, wherein the second electrical double layer is proximal to a surface of fourth electrode, a surface of the fifth electrode, and a surface of the sixth electrode; (p) varying the third phase angle of the third input electric voltage and the fourth phase angle of the fourth input electric voltage over the second range of phase angles; (q) identifying the third phase angle and the fourth phase angle at which a second maximum impedance change occurs; (r) measuring the impedance identified at the third phase angle and the fourth phase angle; and (s) using the measured impedance and phase change at different frequencies to detect a second target analyte or calculate a concentration of the second target analyte by use of a standard calibration curve. In particular embodiments, steps (a)-(j) are performed concurrently with steps (k)-(s).

In certain embodiments, the first range of frequencies and the second range of frequencies are different. In particular embodiments, the first range of phase angles and the second range of phase angles are different. In some embodiments, the first range of frequencies and the second range of frequencies are equal. In specific embodiments, the first range of phase angles and the second range of phase angles are equal.

Exemplary embodiments include a method of detecting or quantifying a target analyte in a sample using a handheld measuring device and a conformal analyte sensor circuit comprising the steps of: (a) applying a first input electric voltage between a first electrode and a second electrode of a conformal analyte sensor circuit; (b) applying a second input electric voltage between a third electrode and the second electrode of the conformal analyte sensor circuit; (c) amplifying an output current flowing from the first electrode and from the third electrode through the second electrode using a programmable gain amplifier; (d)

calculating an impedance by comparing the first input electric voltage and the second input electric voltage to the output current using a programmable microcontroller; and (e) detecting a target analyte or calculating a target analyte concentration from the calculated impedance using a programmable microcontroller.

Exemplary embodiments include a method of detecting or quantifying multiple target analytes in a sample using a handheld measuring device and a conformal analyte sensor circuit comprising the steps of: (a) applying a first input electric voltage between a first electrode and a second electrode of a conformal analyte sensor circuit; (b) applying a second input electric voltage between a third electrode and the second electrode of the conformal analyte sensor circuit; (c) shifting an angular orientation of an electric field of the second input electric voltage; (d) amplifying an output current flowing through the first electrode using a programmable gain amplifier; (e) detecting a presence of one or more target analytes by comparing the angular orientation of the electric field to the output current. The types of analytes that can be measured include analytes in liquid or gaseous analytes incorporated into liquid.

In exemplary embodiments, the first input electric voltage and the second input electric voltage have a frequency between 50 Hz and 5,000 Hz. In certain embodiments, the first input electric voltage and the second input electric voltage are sinusoidal, and/or sawtooth waves and/or square waves. In particular embodiments, the first input electric voltage and the second input electric voltage are between 100 mV and 500 mV, or more particularly between 50 mV and 200 mV, or still more particularly between 5 mV and 20 mV.

In specific embodiments, the output current is between 10 pA and 10 mA, or more particularly between 10 pA and 100 nA, or more particularly between 100 nA and 10 mA. In certain embodiments, the output current is amplified by a factor between 1 and 200. Particular embodiments further comprise calculating impedance as a function of frequency by applying a fast Fourier transform and/or calculating impedance as a function of frequency using a Laplace transform. Certain embodiments further comprise calculating impedance as a function of frequency using multi-slice splitting and signal analysis. In particular embodiments, the angular orientation is shifted between 0 and 360 degrees. Specific embodiments further comprise displaying the calculated target analyte concentration. Certain embodiments further comprise displaying the calculated impedance. Particular embodiments further comprise displaying an output on an LCD display. Specific embodiments further comprise displaying an output on a smartphone. Certain embodiments further comprise providing an input using a mini-joystick. Particular embodiments further comprise providing an input using a smartphone. In specific embodiments, the measured impedance is non-faradaic.

In certain embodiments, the conformal analyte sensor circuit comprises: a solid substrate having a top surface, wherein the substrate comprises a porous nanotextured substrate; and a conductive material situated on the top surface of the solid substrate in a circuit design, thereby creating a circuit comprising the first electrode, the second electrode, and the third electrode. In particular embodiments, the porous nanotextured substrate has a porosity of 10×107 to 10×1018 pores/mm2, or more particularly a porosity of 10×1010 to 10×1013 pores/mm2. In specific embodiments, the porous nanotextured substrate is an insulating substrate. In certain embodiments, the porous nanotextured substrate is paper or nitrocellulose. In particular embodiments, the conductive material is conductive ink or semi-conductive ink. In specific embodiments, the semi-conductive ink comprises carbon ink and additives, and in certain embodiments, the conductive ink is carbon, silver, or metal or metal oxide nanoparticle-infused carbon inks.

In particular embodiments, the metal or metal-oxide nanoparticle-infused carbon ink is 1% by volume infused with gold, platinum, tantalum, silver, copper, tin, indium-tin oxide, grapheme, grapheme oxide, zinc oxide, titanium oxide, iron oxide, or molybdenum oxide. In specific embodiments, the circuit is a nonlinear circuit, and in certain embodiments, the circuit is a non-ohmic circuit. Certain embodiments comprise a base electrode surface, and in particular embodiments, the base electrode surface is further coupled to a source circuit. In specific embodiments, the source circuit comprises a potentiostat, and/or a voltage source, and/or a current source.

In certain embodiments, the circuit does not contain a capture ligand or label-molecule. In particular embodiments, the conformal analyte sensor further comprises a redox material.

In exemplary embodiments, the analyte sensor circuit is assembled by a method comprising: (a) providing the solid porous nanotextured substrate; and (b) transferring the analyte sensor circuit design onto the top surface of the porous nanotextured substrate using conductive material. In certain embodiments, transferring the circuit design comprises dip coating. In particular embodiments, the feature resolution of the circuit is up to 100 nanometers/0.1 micron. In specific embodiments, transferring the circuit design comprises embossing. In certain embodiments, the feature resolution of the circuit is up to 100 nanometers/0.1 micron. In particular embodiments, transferring the circuit design comprises designing the circuit on a 3D printer and embossing the circuit onto the substrate. In specific embodiments, the feature resolution of the circuit is up to 100 nanometers/0.1 micron. In certain embodiments, the circuit design comprises masking and lithography. In particular embodiments, the feature resolution of the circuit is 1-10 microns.

Exemplary embodiments include a handheld device for measuring a target analyte comprising: (a) a programmable gain amplifier configured to be operably coupled to a first electrode, a second electrode, and a third electrode; (b) a programmable microcontroller operably coupled to the programmable gain amplifier, the first electrode, the second electrode, and the third electrode; where the programmable microcontroller is operable to apply a first alternating input electric voltage between the first electrode and the second electrode; the programmable microcontroller is operable to apply a second alternating input electric voltage between the third electrode and the second electrode; the programmable gain amplifier is operable to amplify an alternating output current flowing from the first electrode and from the third electrode through the second electrode; the programmable microcontroller is operable to calculate an impedance by comparing the first input electric voltage and the second input electric voltage to the measured output current; and the programmable microcontroller is operable to calculate a target analyte concentration from the calculated impedance.

Exemplary embodiments include a handheld device for measuring a target analyte comprising: (a) a programmable gain amplifier configured to be operably coupled to a first electrode, a second electrode, and a third electrode; (b) a programmable microcontroller operably coupled to the programmable gain amplifier, the first electrode, the second electrode, and the third electrode; where the programmable microcontroller is operable to apply a first alternating input electric voltage between the first electrode and the second electrode; the programmable microcontroller is operable to apply a second alternating input electric voltage between the third electrode and the second electrode; the programmable gain amplifier is operable to shift the angular orientation of an electric field of the second alternating input electric voltage; the programmable gain amplifier is operable to amplify an alternating output current flowing through the third electrode; the programmable microcontroller is operable to calculate an amplitude of the alternating output current; and the programmable microcontroller is operable to detect a presence of one or more target analytes by comparing the angular orientation to the amplitude of the alternating output current.

In certain embodiments of the handheld measuring device, the programmable microcontroller is operable to apply the first alternating input electric voltage and the second alternating input electric voltage that have a frequency between 50 Hz and 1,000 Hz. In particular embodiments, the programmable microcontroller is operable to apply the first alternating input electric voltage and the second alternating input electric voltage that are sinusoidal. In specific embodiments, the programmable microcontroller is operable to apply the first alternating input electric voltage and the second alternating input electric voltage that are sawtooth waves. In certain embodiments, the programmable microcontroller is operable to apply the first alternating input electric voltage and the second alternating input electric voltage that are square waves. In particular embodiments, the programmable gain amplifier has a variable gain of between 1 and 200. In specific embodiments, the microcontroller is operable to apply a first alternating input electric voltage and a second alternating input electric voltage of between 5 mV and 500 mV. In certain embodiments, the handheld measuring device is operable to detect an output current of 10 pA or greater. In particular embodiments, the programmable microcontroller comprises an analog to digital converter and a digital to analog converter. In specific embodiments, the programmable microcontroller is operable to apply a fast Fourier transform to the input electric voltage and output current to calculate impedance as a function of frequency. In certain embodiments, the programmable microcontroller is operable to apply a Laplace transform to the input electric voltage and output current to calculate impedance as a function of frequency. In particular embodiments, the programmable microcontroller is operable to use multi-slice splitting and signal analysis to determine a frequency at which the impedance change is at a maximum or minimum. In specific embodiments, the programmable microcontroller is operable to shift the angular orientation from 0 to 360 degrees.

Certain embodiments further comprise a liquid crystal display operably coupled to the programmable microcontroller; a mini-joystick operably coupled to the programmable microcontroller; where the mini-joystick is operable to allow users to provide input; and the liquid crystal display is capable of displaying output data. Particular embodiments further comprise a smartphone operably coupled to the programmable microcontroller; where the smartphone is operable to allow users to provide input; and the smartphone is capable of displaying output data. In specific embodiments, the output data comprises the target analyte concentration. In certain embodiments, the output data comprises the impedance. In specific embodiments, the handheld measuring device does not contain a redox probe.

Exemplary embodiments include a method of calibrating a handheld measuring device by testing a plurality of solutions having known target analyte concentrations comprising: (a) applying a first input electric voltage between a first electrode and a second electrode for each of the plurality of solutions; (b) applying a second input electric voltage between a third electrode and a second electrode for each of the plurality of solutions; (c) amplifying an output current flowing from the first electrode and from the third electrode through the second electrode using a programmable gain amplifier; (d) calculating an impedance for each of the plurality of solutions by comparing the first input electric voltage and the second input electric voltage to the output current using a programmable microcontroller; (e) calculating coefficients of the equation $z_i = b_1 x^2 + b_2 x + c$, wherein $z_i$ is the impedance, x is the known target analyte concentrations, and $b_1$, $b_2$, and c are the coefficients.

Exemplary embodiments include a kit comprising a conformal circuit and a handheld measuring device as described herein.

In some embodiments, the handheld potentiometer comprises an LCD screen, mini-joystick, a first electrode port, a second electrode port, a third electrode port, programmable microcontroller, and programmable gain amplifier. In other embodiments, the handheld potentiometer comprises a smartphone, cable, potentiostat adaptor, first electrode port, second electrode port, third electrode port, programmable microcontroller, and programmable gain amplifier. In some embodiments, the handheld potentiometer comprises a programmable microprocessor instead of a programmable microcontroller.

In some embodiments, the handheld device for measuring a target analyte comprises (a) a programmable gain amplifier configured to be operably coupled to a first electrode, a second electrode, and a third electrode (b) a programmable microcontroller operably coupled to the programmable gain amplifier, the first electrode, the second electrode, and the third electrode wherein the programmable microcontroller is operable to apply an alternating input electric voltage between the first electrode and the second electrode and an alternating input electric voltage between the third electrode and the second electrode; the programmable gain amplifier is operable to amplify an alternating output current flowing from the first electrode through the second electrode and amplify an alternating output current flowing from the third electrode through the second electrode; the programmable microcontroller is operable to calculate an impedance by comparing the input electric voltages to the measured output currents; and the programmable microcontroller is operable to calculate a target analyte concentration from the calculated impedance.

In some embodiments, the handheld device for measuring a target analyte comprises (a) a programmable gain amplifier configured to be operably coupled to a first electrode, a second electrode, and a third electrode (b) a programmable microcontroller operably coupled to the programmable gain amplifier, the first electrode, the second electrode, and the third electrode wherein the programmable microcontroller is operable to apply an alternating input electric voltage between the first electrode and the second electrode and an alternating input electric voltage between the third electrode and the second electrode; the programmable microcontroller is operable to vary an orientation of the electric field between the third and the reference electrode; the programmable gain amplifier is operable to determine the current response at the third electrode; and the programmable microcontroller is operable to determine the presence of a plurality of target analytes based upon the current response compared to the angle of orientation.

In some embodiments, the third-second electrode electric field has the same orientation as the first-reference electrode electric field. In some embodiments, the third-second electrode electric field is perpendicular to the orientation of the first-second electrode electric field. In some embodiments, the orientation of the third-second electrode electric field is varied from 0 to 360 degrees in relation to the first-second electrode electric field. In some embodiments, the third electrode is parallel to the first and second electrodes. In other embodiments, the third electrode is perpendicular to the first and second electrodes. In some embodiments, the programmable microcontroller is operable to apply an input electric voltage between the first electrode and the second electrode and between the third electrode and the second electrode that has a frequency between 50 Hz and 1,000 Hz. In some embodiments, the programmable microcontroller is operable to apply an input electric voltage that is sinusoidal. In some embodiments, the programmable microcontroller is operable to apply an input electric voltage that is a sawtooth wave. In some embodiments, the programmable microcontroller is operable to apply an input electric voltage that is a square wave. In some embodiments, the programmable gain amplifier has a variable gain of between 1 and 200. In some embodiments, the microcontroller is operable to apply an input electric voltage of between 10 mV and 2 V. In some embodiments, the handheld measuring device is operable to detect an output current 10 pA or greater. In some embodiments, the programmable microcontroller comprises an analog to digital converter and a digital to analog converter. In some embodiments, the programmable microcontroller is capable of measuring a difference in phase between the input electric voltages and the output currents. In some embodiments, the programmable microcontroller is operable to apply a fast Fourier transform to the input electric voltages and output currents to calculate impedance as a function of frequency. In some embodiments, the programmable microcontroller is operable to apply a Laplace transform to the input electric voltages and output currents to calculate impedance as a function of frequency. In some embodiments, the programmable microcontroller is operable to use multi-slice splitting and signal analysis to determine a frequency at which the impedance change is at a maximum or minimum. In some embodiments, the device further comprises a liquid crystal display operably coupled to the programmable microcontroller; a mini-joystick operably coupled to the programmable microcontroller; wherein the mini-joystick is operable to allow users to provide input; and the liquid crystal display is capable of displaying output data. In some embodiments, the device further comprises a smartphone operably coupled to the programmable microcontroller; wherein the smartphone is operable to allow users to provide input; and the smartphone is capable of displaying output data. In some embodiments, the output data comprises the target analyte concentration(s). In some embodiments, the handheld measuring device does not contain a redox probe.

The conformal analyte sensor circuit comprises a porous nanotextured substrate and a conductive material situated on the top surface of the solid substrate in a circuit design, thereby creating a circuit comprising a first electrode, a second electrode, and a third electrode. The porosity of the nanotextured substrate is determined by the target analyte to be measured. In some embodiments, the porous nanotextured substrate has a porosity at or between $10 \times 10^7$ and $10 \times 10^{18}$ pores/mm$^2$. In some embodiments, the porous nanotextured substrate has a porosity at or between $10 \times 10^{10}$ and $10 \times 10^{13}$ pores/mm$^2$. In some embodiments, the porous nanotextured substrate is an insulating substrate. In some embodiments, the porous nanotextured substrate is paper or nitrocellulose.

The conductive material may be any appropriate material known to those of skill in the art. In some embodiments, the conductive material is conductive ink or semi-conductive ink. In some embodiments, the semi-conductive ink comprises carbon ink and additives. In some embodiments, the conductive ink is carbon, silver, or metal or metal oxide nanoparticle-infused carbon inks. In some embodiments, the metal or metal-oxide nanoparticle-infused carbon ink is 1% by volume infused with gold, platinum, tantalum, silver, copper, tin, indium-tin oxide, grapheme, grapheme oxide, zinc oxide, titanium oxide, iron oxide, or molybdenum oxide.

The circuit may be a nonlinear circuit or a non-ohmic circuit. In some embodiments, the circuit is further defined as a base electrode surface. In some embodiments, the base electrode surface is further connected to a source current. In some embodiments, the source current is a potentiostat. In some embodiments, the source circuit is a voltage source. In some embodiments, the source circuit is a current source. In some embodiments, the circuit does not contain a capture ligand or label-molecule. In some embodiments, the conformal analyte sensor further comprises a redox material.

In some embodiments, any of the conformal analyst sensor circuits disclosed herein is assembled by a method comprising (a) providing the solid porous nanotextured substrate; and (b) transferring the analyte sensor circuit design onto the top surface of the porous nanotextured substrate using conductive material. In some embodiments, transferring the circuit design comprises dip coating. In such embodiments, the feature resolution of the circuit is up to 100 nanometers/0.1 micron. In some embodiments, transferring the circuit design comprises embossing. In such embodiments, the feature resolution of the circuit is up to 100 nanometers/0.1 micron. In some embodiments, transferring the circuit design comprises designing the circuit on a 3D printer and embossing the circuit onto the substrate. In such embodiments, the feature resolution of the circuit is up to 100 nanometers/0.1 micron. In some embodiments, transferring the circuit design comprises masking and lithography. In such embodiments, the feature resolution of the circuit is 1-10 microns.

In some embodiments, disclosed is a kit comprising any of the conformal analyst sensor circuits disclosed herein and any of the handheld measuring devices disclosed herein.

The handheld potentiostats and porous nanotextured conformal circuits disclosed herein may be used separately or in combination to detect and/or quantify a target analyte. In some embodiments, disclosed is a method of detecting a target analyte comprising spotting a sample on a disclosed conformal analyte sensor circuit, wherein the sample wicks through the porous nanotextured substrate and the circuit design, attaching the conformal analyte sensor circuit to a source circuit, and detecting the target analyte in the sample with a source circuit. In some embodiments, the source circuit is a potentiostat. In some embodiments, the source circuit is a voltage source. In some embodiments, the source circuit is a current source. In some embodiments, the sample contains 1-10 µl of a fluid. In some embodiments, the target analyte is a protein, DNA, RNA, SNP, small molecules, pathogens heavy metal ions, or physiological ions. In some embodiments, the sample is not labeled. In some embodiments, detecting the target analyte comprises detecting an electrical change.

In some embodiments, disclosed is a method of detecting or quantifying a target analyte in a sample using a handheld measuring device comprising the steps of (a) applying input electric voltages between a first electrode and a second electrode and between a third electrode and the second electrode, (b) amplifying output currents flowing from the first electrode through the second electrode and flowing from the third electrode through the second electrode using a programmable gain amplifier, (c) calculating an impedance by comparing the input electric voltages to the output currents using a programmable microcontroller, and (d) calculating a target analyte concentration from the calculated impedance using a programmable microcontroller.

In some embodiments, disclosed is a method of detecting or quantifying a target analyte in a sample using a handheld measuring device comprising the steps of (a) applying input electric voltages between a first electrode and a second electrode and between a third electrode and the second electrode, (b) amplifying output currents flowing from the first electrode through the second electrode and flowing from the third electrode through the second electrode using a programmable gain amplifier, (c) shifting an orientation of an electric field between the third electrode and the second electrode, (d) measuring a current response at the third electrode using a programmable microcontroller, and (d) determining an identity of a target analyte by comparing the current response to the orientation using a programmable microcontroller.

In some embodiments, the third electrode is parallel to the first electrode and the second electrode. In some embodiments, the third electrode is perpendicular to the first electrode and the second electrode. In some embodiments, the electric field of the third-second electrodes is oriented ninety degrees from the electric field of the first-second electrodes. In some embodiments, the third-reference electrode electric field has the same orientation as the first-second electrode electric field. In some embodiments, the orientation of the third-second electrode electric field is varied from 0 to 360 degrees in relation to the first-second electrode electric field. In some embodiments, the input electric voltages have a frequency between 50 Hz and 1,000 Hz. In some embodiments, the input electric voltages are sinusoidal. In some embodiments, the input electric voltages are sawtooth waves. In some embodiments, the input electric voltages are square waves. In some embodiments, the input electric voltages are between 100 mV and 500 mV. In some embodiments, the input electric voltages are between 50 mV and 200 mV. In some embodiments, the input electric voltages are between 5 mV and 20 mV. In some embodiments, the output currents are between 10 pA and 10 mA. In some embodiments, the output currents are between 10 pA and 100 nA. In some embodiments, the output currents are between 100 nA and 10 mA. In some embodiments, the output currents are amplified by a factor between 1 and 200. In some embodiments, the method further comprises calculating impedance as a function of frequency by applying a fast Fourier transform and or a Laplace transform. In some embodiments, the method further comprises calculating impedance as a function of frequency using multi-slice splitting and signal analysis. In some embodiments, the method further comprises displaying the calculated target analyte concentration. In some embodiments, the method further comprises displaying an output on an LCD display. In some embodiments, the method further comprises displaying an output on a smartphone. In some embodiments, the method further comprises providing an input using a mini-joystick. In some embodiments, the method further comprises providing an input using a smartphone. In some embodiments, the measured impedance is non-faradaic.

In some embodiments, disclosed is a method of detecting or quantifying a target analyte in a sample using a handheld measuring device comprising the steps of (a) applying input electric voltages between a first electrode and a second electrode and between an third electrode and the second electrode, (b) amplifying output currents flowing from the first electrode through the second electrode and flowing from the third electrode through the second electrode using a programmable gain amplifier, (c) calculating a difference in a phase of the output current to the phase of first input electric voltage and the phase of the second input electric voltage using a programmable microcontroller, and (d) detecting a presence of one or more target analytes by determining maximum differences in the phase of the output current using a programmable microcontroller. In some embodiments, the input electric voltages have a frequency between 50 Hz and 1,000 Hz. In some embodiments, the input electric voltages are sinusoidal. In some embodiments, the input electric voltages are sawtooth waves. In some embodiments, the input electric voltages are square waves. In some embodiments, the input electric voltages are between 100 mV and 500 mV. In some embodiments, the input electric voltages are between 50 mV and 200 mV. In some embodiments, the input electric voltages are between 5 mV and 20 mV. In some embodiments, the output currents are between 10 pA and 10 mA. In some embodiments, the output currents are between 10 pA and 100 nA. In some embodiments, the output currents are between 100 nA and 10 mA. In some embodiments, the output currents are amplified by a factor between 1 and 200. In some embodiments, the method further comprises displaying the calculated target analyte concentration. In some embodiments, the method further comprises displaying an output on an LCD display. In some embodiments, the method further comprises displaying an output on a smartphone. In some embodiments, the method further comprises providing an input using a mini-joystick. In some embodiments, the method further comprises providing an input using a smartphone.

The handheld potentiometer detects concentrations of a target analyte by applying alternating voltages between the first and second electrodes and between the third and second electrodes. The alternating voltage applied between the first and second electrodes differs in phase from the voltage applied between the third and second electrodes by 90 degrees. The applied alternating voltages result in a current flowing from the first electrode through the second electrode and a current flowing from the third electrode through the second electrode. The resulting currents are amplified by a programmable amplifier and passed onto the programmable microcontroller. The programmable microcontroller compares the applied voltages to the resulting currents to calculate the impedance of the tested sample. The impedance is used to calculate the concentration of the target analyte in the tested sample. In some embodiments, to perform testing of a target analyte using the handheld potentiometer, the handheld potentiometer is first calibrated by testing and calculating the impedance of samples containing known quantities of the target analyte. In some embodiments, the system applies voltages of varying frequencies and determines the frequency at which the maximum impedance change occurs for a particular tested analyte.

The claimed system may perform non-Faradaic electrochemical impedance spectroscopy (EIS) by testing samples without using a redox electrode.

In some embodiments, disclosed herein is a method of calibrating a handheld measuring device by testing a plurality of solutions having known target analyte concentrations comprising (a) applying input electric voltages between a first electrode and a second electrode and between a third electrode and a second electrode for each of the plurality of solutions, (b) calculating an impedance for each of the plurality of solutions by comparing the input electric voltages to the output currents using a programmable microcontroller, and (c) calculating coefficients of the equation $z_i=b_1x^2+b_2x+c$, wherein $z_i$ is the impedance, x is the known target analyte concentrations, and b1, b2, and c are the coefficients.

Exemplary embodiments may be used in conjunction with samples as provided below.

A. Samples

Samples can come from a wide variety of sources. In one aspect, the sample is derived from a living organism, including a plant, animal (veterinary uses) or human. Such samples may involve solid material such as feces or tissues (including biopsies), tissue extracts, or fluids, including body fluids such as saliva, sputum, tears, blood, serum, plasma, urine, exudate, transudate, spinal fluid, semen or nasal discharge. Such samples may be solubilized or diluted, as needed, to perform the assays of the present invention. Solvents for use in solubilizing or diluting samples include water, acetone, methanol, toluene, ethanol or others.

Other samples, are manufactured, industrial or environmental, and may or may not contain living cells or organisms. Such sample may include soil, water, foodstuffs, alcoholic beverages, building products, bulk chemicals or reagents, including drugs. Again, such samples may be solubilized or diluted, as needed, to perform the assays of the present invention.

B. Targets

Autoimmune Antigens or Antibodies Thereto. Autoimmune diseases can be generally classified as antibody-mediated, T-cell mediated, or a combination of antibody-mediated and T-cell mediated. Thus, antibodies or T-cell receptors can be identified with specificity to a variety of endogenous antigens. Such auto-antibodies (e.g., anti-nuclear antibodies) may be implicated in various disease including insulin-dependent (type I) diabetes mellitus, rheumatoid arthritis, multiple sclerosis, systemic lupus erythematosus (SLE), and inflammatory bowel disease (i.e., Crohn's disease and ulcerative colitis). Other autoimmune diseases include, without limitation, alopecia areata, acquired hemophilia, ankylosing spondylitis, antiphospholipid syndrome, autoimmune hepatitis, autoimmune hemolytic anemia, cardiomyopathy, celiac sprue dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia, fibromyositis, Guillain-Barr syndrome, idiopathic pulmonary fibrosis, idiopathic thrombocytopenic purpura, IgA nephropathy, juvenile arthritis, lichen planus, myasthenia gravis, polyarteritis nodosa, polychondritis, polyglandular syndromes, dermatomyositis, primary agammaglobulinemia, primary biliary cirrhosis, psoriasis, Raynaud's phenomena, Reiter's syndrome, sarcoidosis, stiff-man syndrome, Takayasu arthritis, temporal arteritis/giant cell arteritis, uveitis, vasculitis, and vitiligo.

In particular autoimmune diseases, antibodies to self antigens are frequently observed. For example for systemic lupus erythematosus autoantibodies have been described to single-stranded and double-stranded DNA or RNA (Vallin et al., 1999; Hoet et al., 1999; yen Venrooij, 1990). The levels of autoantibodies found in the serum of autoimmune patients very often are found to correlate with disease severity. The pattern of autoantibodies that arise, e.g., in human SLE, suggest that intact macromolecular particles, such as RNA- or DNA-containing complexes, could themselves be immunogenic and anti-nucleic acid antibodies could themselves arise (Lotz et al., 1992; Mohan et al., 1993). Such DNA or RNA released from, e.g., apoptotic cells or DNA- or RNA-containing microbes present in serum of autoimmune patients, could be responsible for inflammation that contributes to the autoimmune disease (Fatenejad, 1994; Malmegrim et al., 2002; Newkirk et al., 2001). Indeed CpG-containing sequences could be identified from SLE serum that induces an efficient immune response dominated by IFN-α. secretion that is thought to contribute the development of to autoimmune diseases (Magnusson et al., 2001; Ronnblom et al., 2001). In addition, the epitopes for anti-RNA antibodies could be identified and are composed of G,U-rich sequences (Tsai et al., 1992; Tsai et al., 1993). G,U-rich sequences appear to be natural ligands for TLR7 and TLR8 and, therefore, can mediate immune stimulatory responses that in principle could contribute to autoimmune diseases or the development of autoimmune diseases (PCT/US03/10406).

Specific antigens to which auto-antibodies are produced include β-glycoprotein, cardiolipin, CCP, CENP, GBM, gliadin, Jo-1, LKM1, La, MPO, Parietal Cell antigens, PR3, Ro, SS-B/La, SS-A/Ro, Scl-70, Sm, sperm transglutaminase, TPO and U1RNP.

Infectious Agents.

Infections refer to any condition in which there is an abnormal collection or population of viable intracellular or extracellular microbes in a subject. Various types of microbes can cause infection, including microbes that are bacteria, microbes that are viruses, microbes that are fungi, and microbes that are parasites. Detection of antigens or nucleic acids associated with these microbes, or antibodies thereto, is contemplated in accordance with the present invention.

Bacteria include, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans,* other viridans streptococci, peptostreptococci, other related species of streptococci, enterococci such as *Enterococcus faecalis, Enterococcus faecium,* staphylococci, such as *Staphylococcus epidermidis, Staphylococcus aureus, Hemophilus influenzae,* pseudomonas species such as *Pseudomonas aeruginosa, Pseudomonas pseudomallei, Pseudomonas mallei,* brucellas such as *Brucella melitensis, Brucella suis, Brucella abortus, Bordetella pertussis, Borellia* species, such as *Borellia burgedorferi Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi,* etc. *Listeria monocytogenes, Nocordia asteroides, Bacteroides* species, *Actinomycetes* species, *Treponema pallidum, Leptospirosa* species, *Haemophilus* species, *Helicobacter* species, including *Helicobacter pylori, Treponema* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteroides* and *Legionella* species, *Shigella* species, *Mycobacterium* species (e.g., *Mycobacterium tuberculosis, Mycobacterium bovis* or other mycobacteria infections), *Mycobacterium avium* complex (MAC), *Mycobacterium marinum, Mycobacterium fortui-*

*tum, Mycobacterium kansaii, Yersinia* infections (e.g., *Yersinia pestis, Yersinia enterocolitica* or *Yersinia pseudotuberculosis*) and the like.

In addition, the invention contemplates detection of parasitic organisms such as *Cryptosporidium, Entamoeba, Plasmodium* spp., such as *Plasmodium falciparum, Plasmodium malariae, Plasmodium ovale*, and *Plasmodium vivax* and *Toxoplasma gondii, Giardia, Leishmania, Trypanasoma, Trichomonas, Naegleria, Isospora belli, Trichomonas vaginalis, Wunchereria, Ascaris, Schistosoma* species, *Cyclospora* species, for example, and for *Chlamydia trachomatis* and other *Chlamydia* infections such as *Chlamydia psittaci*, or *Chlamydia pneumoniae*, for example. Of course it is understood that the invention may be used on any pathogen against which an effective antibody can be made.

Fungal and other mycotic pathogens (some of which are described in Human Mycoses (1979; Opportunistic Mycoses of Man and Other Animals (1989); and Scrip's Antifungal Report (1992), are also contemplated as a target of diagnosis. Fungi disease contemplated in the context of the invention include, but are not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, Tinea barbae, Tinea capitis, Tinea corporis, Tinea cruris, Tinea favosa, Tinea imbricata, Tinea manuum, Tinea nigra (palmaris), Tinea pedis, Tinea unguium, Torulopsosis, Trichomycosis axillaris, White piedra, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystis pneumonia, Pythiosis, Sporotrichosis, and Torulopsosis, and their synonyms, some of which may be fatal. Known fungal and mycotic pathogens include, but are not limited to, *Absidia* spp., *Actinomadura madurae, Actinomyces* spp., *Alleschería boydii, Alternaria* spp., *Anthopsis deltoidea, Apophysomyces elegans, Arnium leoporinum, Aspergillus* spp., *Aureobasidium pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastrum racemosum, Taeniolella boppii, Torulopsosis* spp., *Trichophyton* spp., *Trichosporon* spp., *Ulocladium chartarum, Wangiella dermatitidis, Xylohypha* spp., *Zygomyetes* spp. and their synonyms. Other fungi that have pathogenic potential include, but are not limited to, *Thermomucor indicae-seudaticae, Radiomyces* spp., and other species of known pathogenic genera.

Examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); unclassified viruses (e.g., the agent of delta hepatitis (thought to be a defective satellite of hepatitis B virus), Hepatitis C; Norwalk and related viruses, and astroviruses); and resipiratory syncytial virus (RSV).

Other medically relevant microorganisms have been described extensively in the literature, e.g., see Medical Microbiology (1983), the entire contents of which is hereby incorporated by reference.

Cancer Antigens.

Many human cancers express cell surface molecule that are specific to the cancer cell, i.e., they are not expressed or expressed in greatly reduced quantity by normal human somatic cells. The role of these antigens in cancerogenesis and cancer progression is often poorly understood, however, independent of their biological functions these antigens are attractive antibody targets for diagnostic applications. Such tumor markers include alpha-feto protein, beta-2-microglobulin, bladder tumor antigen, CA 15-3, CA 19-9, CA 72-4, CA-125, calcitonin, carcinoembryonic antigen, epidermal growth factor receptor, estrogen receptor, human chorionic gonadotropin, Her-2/neu, neuron-specific enolase, NPM22, progesterone receptor, prostate specific antigen, prostate-specific membrane antigen, prostatic acid phosphatase, S-100, TA-90 and thyroglobulin.

Toxins, Metals and Chemicals.

A particular type of chemical or biological agent is a toxin. Toxins can be biological, i.e., produced by an organism. These include toxins that may be used in biological warfare or terrorism, including ricin, anthrax toxin, and botulism toxin. Other toxins are pesticides (insecticides, herbicides; e.g., organophosphates), industrial contaminants (heavy metals, such as cadmium, thallium, copper, zinc, selenium, antimony, nickel, chromium, arsenic, mercury or lead; complex hydrocarbons, include PCBs, and petroleum byproducts; asbestos), and chemical warfare reagents (sarin, soman, cyclosarin, VX, VG, GV, phosgene oxime, nitrogen mustard, sulfur mustard and cyanogen chloride). Table 1 below shows a further list of toxic industrial chemicals (TICs). A specific list of 12 banned persistent organic pollutants includes PCBs, DDT, dioxins, chlordane, furans, hexochlorobenzene, aldrin, mirex, dieldrin, toxaphene, endrin, and heptachlor.

TABLE 1

TICs listed by hazard index

| High | Medium | Low |
|---|---|---|
| Ammonia (CAS# 7664-41-7) | Acetone cyanohydrin (CAS# 75-86-5) | Allyl isothiocyanate (CAS# 57-06-7) |
| Arsine (CAS# 7784-42-1) | Acrolein (CAS# 107-02-8) | Arsenic trichloride (CAS# 7784-34-1) |
| Boron trichloride (CAS#10294-34-5) | Acrylonitrile (CAS# 107-13-1) | Bromine (CAS# 7726-95-6) |
| Boron trifluoride (CAS#7637-07-2) | Allyl alcohol (CAS# 107-18-6) | Bromine chloride (CAS# 13863-41-7) |
| Carbon disulfide (CAS# 75-15-0) | Allylamine (CAS# 107-11-9) | Bromine pentafluoride (CAS# 7789-30-2) |
| Chlorine (CAS# 7782-50-5) | Allyl chlorocarbonate (CAS# 2937-50-0) | Bromine trifluoride (CAS# 7787-71-15) |
| Diborane (CAS# 19287-45-7) | Boron tribromide (CAS# 10294-33-4) | Carbonyl fluoride (CAS# 353-50-4) |
| Ethylene oxide (CAS# 75-21-8) | Carbon monoxide (CAS# 630-08-0) | Chlorine pentafluoride (CAS# 13637-63-3) |
| Fluorine (CAS# 7782-41-4) | Carbonyl sulfide (CAS# 463-58-1) | Chlorine trifluoride (CAS# 7790-91-2) |
| Formaldehyde (CAS# 50-00-0) | Chloroacetone (CAS# 78-95-5) | Chloroacetaldehyde (CAS# 107-20-0) |
| Hydrogen bromide (CAS# 10035-10-6) | Chloroacetonitrile (CAS# 7790-94-5) | Chloroacetyl chloride (CAS# 79-04-9) |
| Hydrogen chloride (CAS# 7647-01-0) | Chlorosulfonic acid (CAS# 7790-94-5) | Crotonaldehyde (CAS# 123-73-9) |
| Hydrogen cyanide (CAS#74-90-8) | Diketene (CAS# 674-82-8) | Cyanogen chloride (CAS# 506-77-4) |
| Hydrogen fluoride (CAS# 7664-39-3) | 1,2-Dimethylhydrazine (CAS# 540-73-8) | Dimethyl sulfate (CAS# 77-78-1) |
| Hydrogen sulfide (CAS# 7783-0604) | Ethylene dibromide (CAS# 106-93-4) | Diphenylmethane-4.4'-diisocyanate (CAS# 101-68-8) |
| Nitric acid, fuming (CAS# 7697-37-2) | Hydrogen selenide (CAS# 7783-07-5) | Ethyl chlroroformate (CAS# 541-41-13) |
| Phosgene (CAS# 75-44-5) | Methanesulfonyl chloride (CAS# 124-63-0) | Ethyl chlorothioformate (CAS# 2941-64-2) |
| Phosphorus trichloride (CAS# 7719-12-2) | Methyl bromide (CAS# 74-83-9) | Ethyl phosphonothioic dichloride (CAS# 993-43-1) |
| Sulfur dioxide (CAS# 7446-09-5) | Methyl chloroformate (CAS# 79-22-1) | Ethyl phosphonic dichloride (CAS# 1066-50-8) |
| Sulfuric acid (CAS# 7664-93-9) | Methyl chlorosilane (CAS# 993-00-0) | Ethyleneimine (CAS# 151-56-4) |
| Tungsten hexafluoride (CAS# 7783-82-6) | Methyl hydrazine (CAS# 60-34-4) | Hexachlorocyclopentadiene (CAS# 77-47-4) |
| | Methyl isocyanate (CAS# 624-83-9) | Hydrogen iodide (CAS# 10034-85-2) |
| | Methyl mercaptan (CAS# 74-93-1) | Iron pentacarbonyl (CAS# 13463-40-6) |
| | Nitrogen dioxide (CAS# 10102-44-0) | Isobutyl chloroformate (CAS# 543-27-1) |
| | Phosphine (CAS# 7803-51-2) | Isopropyl chloroformate (CAS# 108-23-6) |
| | Phosphorus oxychloride (CAS# 10025-87-3) | Isopropyl isocyanate (CAS# 1795-48-8) |
| | Phosphorus pentafluoride (CAS# 7647-19-0) | n-Butyl chloroformate (CAS# 592-34-7) |
| | Selenium hexafluoride (CAS# 7783-79-1) | n-Butyl isocyanate (CAS# 111-36-4) |
| | Silicon tetrafluoride (CAS# 7783-61-1) | Nitric oxide (CAS# 10102-43-9) |
| | Stibine (CAS# 7803-52-3) | n-Propyl chloroformate (CAS# 109-61-5) |
| | Sulfur trioxide (CAS# 7446-11-9) | Parathion (CAS#: 56-38-2) |
| | Sulfuryl fluoride (CAS# 2699-79-8) | Perchloromethyl mercaptan (CAS# 594-42-3) |
| | Tellurium hexafluoride (CAS# 7783-80-4) | sec-Butyl chloroformate (CAS# 17462-58-7) |
| | n-Octyl mercaptan (CAS# 111-88-6) | tert-Butyl isocyanate (CAS# 1609-86-5) |
| | Titanium tetrachloride (CAS# 7550-45-0) | Tetraethyl lead (CAS# 78-00-2) |
| | Tricholoroacetyl chloride (CAS# 76-02-8) | Tetraethyl pyrophosphate (CAS# 107-49-3) |
| | Trifluoroacetyl chloride (CAS# 354-32-5) | Tetramethyl lead (CAS# 75-74-1) |
| | | Toluene 2.4-diisocyanate (CAS# 584-84-9) |
| | | Toluene 2.6-diisocyanate (CAS# 91-08-7) |

Plant Products.

In certain embodiments, the present invention will allow one to assess the content of plant materials. For example, one can measure the health of a plant by measuring the nutrient content of the plants' leaves. One can also make decisions about harvesting of crops by assessing the content of fruit or vegetable tissue. For example, in wine-making, the sugar content of grapes is an important factor in determining harvest time. Also, when selecting crops for breeding, identifying plants with various desirable traits (nutrient content, expression of endogenous products or transgenes) is critical.

Drugs.

In another aspect of the invention, the assays maybe used to detect or measure drugs in samples. The drugs may be therapeutic agents, and the assay is designed to assess drug levels in the subject with the goal of optimizing dosage. Alternatively, illicit drugs may be detected, and include alcohol, amphetamines, methamphetamine, MDMA, barbiturates, phenobarbitol, benzodiazepines, cannabis, cocaine, codeine, morphine, cotinine, heroin, LSD, methadone, PCP, or licit drugs banned for particular purposes, such as sporting events, including anabolic steroids, hormones (EPO, hGH, IGF-1, hCG, insulin, corticotrophins). β2 agonists, anti-estrogens, diuretics, stimulants, and glucocorticosteroids.

Lipids.

Lipids are biologically relevant targets for assays of the present invention. For example, the ability to detect and quantitate lipids in the blood can serve to assess risk of atherosclerotic disease, as well as to monitor the efficacy of therapy therefore. Thus, LDL, HDL and triglyceride measurements are of use.

Sugars.

While assessing sugar levels may be of general medical interest, sugars are particularly relevant to diabetes management and therapy. Other sugars of relevance include those produced by bacteria and fungi in biofilm formation, and those produced during food or beverage production.

Nucleic Acids.

Nucleic acids are significant biological targets for determining the health status of subjects. Nucleic acids of interest include genes (genomic sequences), mRNA (transcripts), miRNAs, or fragments thereof. The nucleic acids may be endogenous to the subject, such as those molecules that may be elevated or decreased in disease states, nor exogenous, such as those of a pathogen (virus, bacteria, parasite) present in the subject (discussed above).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13 A table listing various species of target analytes system and associated system configurations.

FIG. 14 A graph of a change in impedance versus concentration of lipopolysaccharide.

DESCRIPTION OF ILLUSTRATIVE EMBODIMENTS

The conformal circuits disclosed herein leverage the surface roughness that exists at the nanoscale on paper and other nanoporous substrates for designing conformal electric circuits. Circuit parameters such as current and impedance are modulated when the circuit elements are modulated due to the detection of biomolecules through a single step immunoassay format. This technology can be applied towards detecting and quantifying a variety of target analytes, including but not limited to proteins, DNA, RNA, SNP, and a diverse range of biomolecules.

Figure 1:
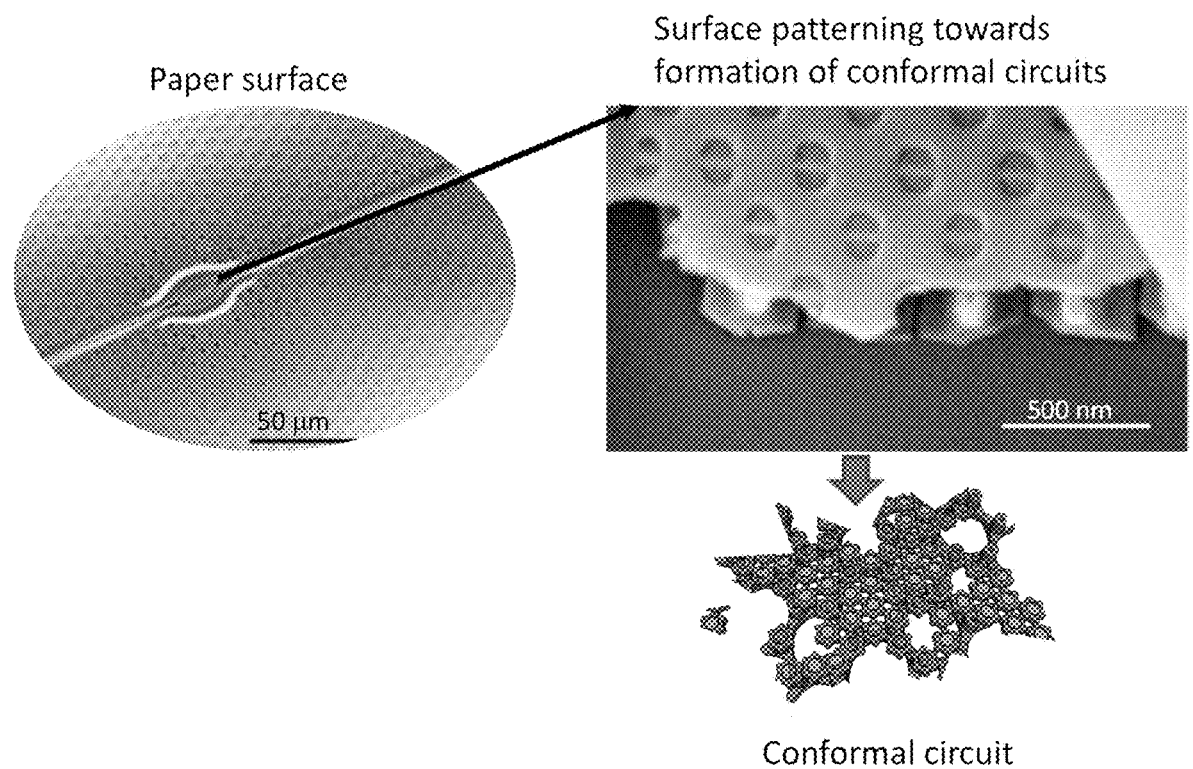
FIG. 1 High resolution optical micrograph demonstrating the surface porosity and interaction between the pores and the electrode surfaces, including a scanning electron micrograph showing conformal feature generation between the electrode and the surrounding matrix with a schematic rendering of the interaction between the measurement entity and the surrounding matrix.

In some embodiments, disclosed herein are conformal circuits comprising a solid substrate having a top surface, wherein the substrate comprises porous nanotextured substrate and a conductive material situated on the top surface of the solid substrate in a circuit design, thereby creating a circuit. Also disclosed are methods of making the same, as well as methods of detecting and/or quantifying a variety of target analytes using the same. FIG. 1 depicts an example design of such a conformal circuit.

These conformal circuits are developed using a combination of track etching and conductive ink deposition to create nonlinear and non-ohmic circuits. Three types of circuits are generated: (a) impedance-based resistive capacitive (RC) coupled circuits, (b) diode-based circuits, and (c) transistor-based circuits. The RC circuits work on the principle of electrochemical impedance spectroscopy, and the diode and transistor circuits are biased by an AC voltage source resulting in changes to current characteristics as a function of detection of species of interest.

The conformal circuits disclosed herein may have an electrode that is conducting, semi-conducting, or semi-insulating. An increase in conductivity is suitable for achieving increased sensitivity in the impedance measurement format. In the diode and transistor format, semi-conducting/semi-insulating materials are used to obtain adequate barrier potential to obtain the appropriate threshold gating/gate current characteristics. For diode performance, the material combination is used to obtain barrier potentials mimicking silicon of up to 0.7 V. For transistor performance, barrier potentials between 0.2 and 0.7 are generated.

The conformal circuits disclosed herein generate electrical changes, as opposed to electrochemical changes. In particular, the conformal circuits disclosed herein generate electrical/electrochemical changes without the use of a reduction-oxidation probe changes, as opposed to electrochemical changes mediated through a redox electrode. The use of a redox probe for electrochemical detection produces irreversible changes to the biomolecule resulting in indirect and modified detection that is not representative of the biomolecules. Thus, this capability is achieved by tailoring the deposition of the conductive material onto the nanoporous substrate. In addition, both passive and active sensing are specifically contemplated.

The conformal circuit and detection devices disclosed herein can be designed to detect quantitatively (e.g., an EIS electronic reader). In addition, the system can be designed to detect a single analyte using a single circuit or multiple analytes using separate circuits, which may be the same or different, depending on the variety of analytes being detected and/or analyzed.

A. Detection Devices

A variety of electrical components can be attached to the electrically conductive material pathways in order to detect and quantify the target analyte. Non-limiting examples of electronic components include integrated circuits, resistors, capacitors, transistors, diodes, mechanical switches, batteries, and external power sources, non-limiting examples of batteries include button cell batteries, and non-limiting examples of external power source include an AC voltage source. The electrical components can be attached using, e.g., known adhesives. In some embodiments, the conformal circuits discussed in detail above can be coupled to a source circuit for the purpose of detecting the biomolecule. In particular embodiments, the conformal circuit can be coupled to potentiostats, voltage sources, current sources, or operational amplifier circuits for doing a wide range of simple and complex mathematical operations, addition, subtraction, integration, and differentiation.

Impedance spectroscopy is a widely used three electrode electrochemical technique for studying material binding efficiency on electrodes. Recently, innovative changes to classical electrochemical impedance spectroscopy have made it suitable for applications to biomedical studies. These modifications demand application of very low voltages and detection at very small currents, both of which fall into the noise threshold of existing devices. In addition, most currently available market potentiostats require additional equipment, such as a computer, and detailed user input, making it difficult for point-of-care implementation. Further, currently available market potentiostats apply a single input voltage between electrodes, providing reduced specificity of detected target analytes.

Disclosed herein are customizable handheld potentiostats devices for performing electrochemical impedance spectroscopy using a three electrode configuration at fixed and variable frequencies. The novel technique used in the disclosed device reduces noise effects and achieves sensitive detection, and the components used are programmable and highly customizable to the desired application. Consequently, this achieves maximum performance efficiency from the device by programming it to function best in the desired range of operation for the particular desired task. In addition, the disclosed device applies two orthogonal input voltages, improving the specificity of detected target analytes.

In the devices disclosed herein, impedance spectroscopy is used to detect and quantify binding activity on an electrode surface. The binding of biomolecules to an electrode surface causes a change in current flow, which can be used to identify and quantify the biomolecule being bound. The detection threshold for the device is approximately in the femtomolar or femtogram/mL concentration ranges, but it can be in the attogram/ml range for some biomolecules.

Figure 2:
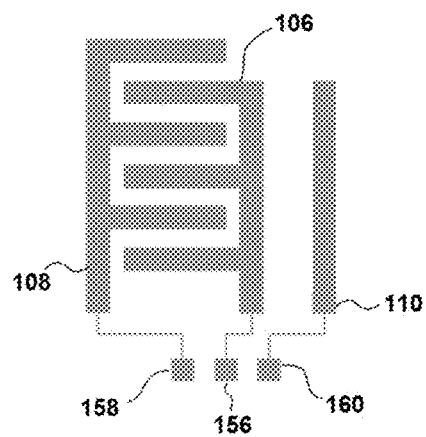
FIG. 2 A schematic representation of an electrode configuration with a third electrode parallel to a first electrode and a second electrode.
Figure 3:
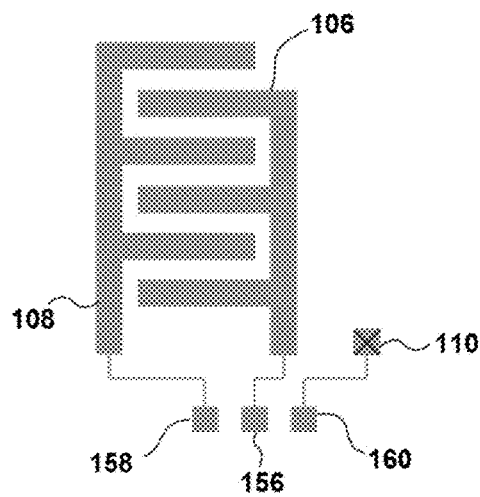
FIG. 3 A schematic representation of an electrode configuration with a third electrode perpendicular to a first electrode and a second electrode FIG. 4 A schematic representation of an electrical double layer and electrode surface.

Exemplary embodiments disclosed herein comprise a first electrode 108, a second electrode 106, and a third electrode 110. In certain embodiments, the first, second and third electrodes 108, 106 and 110 are planar. In exemplary embodiments, first and second electrodes 108 and 106 are disposed parallel to each other in an X-Y plane. In some embodiments, third electrode 110 is parallel to first and second electrodes 108 and 106, as shown in FIG. 2. In other embodiments, third electrode 110 is disposed perpendicular to first and second electrodes 108 and 106, as shown in FIG. 3. In exemplary embodiments, first, second and third electrodes, 108, 106 and 110 may be deposited on a porous nanotextured substrate as shown in FIG. 1 to form a conformal circuit.

Figure 4:
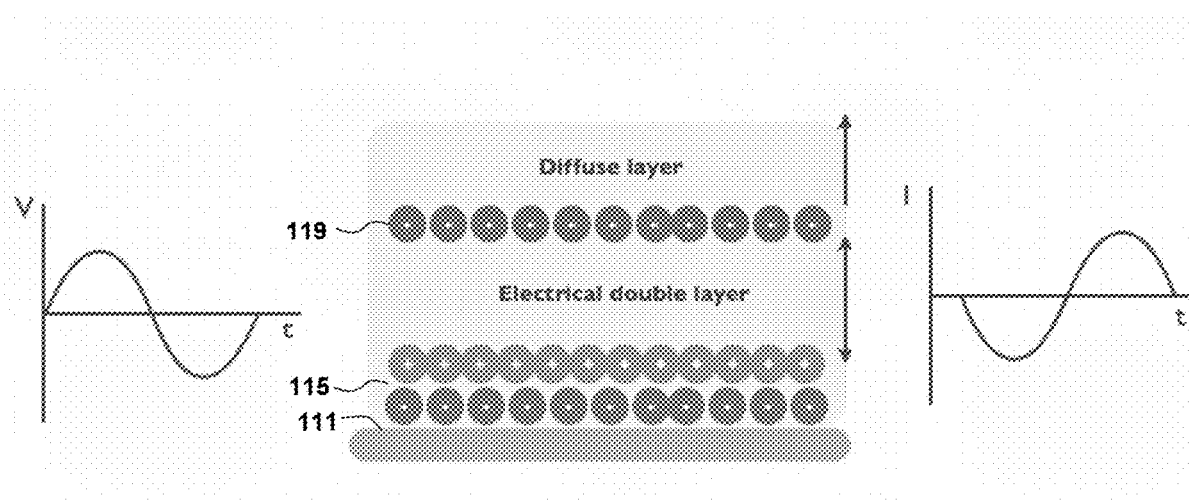

During operation, AC voltages can be applied at terminals 158, 156 and 160 for first, second, and third electrodes 108, 106 and 110 respectively. The AC voltage may be a sinusoidal, sawtooth, or square wave signal. The resulting currents flowing from the first electrode through the second electrode terminal and from the third electrode through the second electrode terminal can then be measured. Referring now to FIG. 4, when a conductive solution is present at the electrode surface and a voltage is applied to the electrodes, a capacitive electrical double layer 115 is formed in the solution near an electrode surface 111, e.g., between the electrode surface and a diffuse layer 119. As properties (e.g., the phase angle, frequency or amplitude) of the applied voltage or voltages change, the distance between electrical double layer 115 and electrode surface 111 also changes. The properties of the applied voltage(s) can be manipulated, and output responses (e.g., current) from electrical double layer 115 can be measured via Helmholtz probing to determine properties of the conductive solution (e.g., the identification or concentration of an analyte in the solution).

In particular embodiments, a first electric field can be applied to first and second electrodes 106 and 108, while a second electric field is applied to second and third electrodes 108 and 110. In particular embodiments, the region within electrical double layer 115 where the maximal change to the measured charge occurs (in a capacitance format) can be identified. This region can then be used to interpret the type of molecule being interrogated. Virtual slicing (with sub-nanometer resolution scanning step) of electrical double layer 115 can be accomplished using a scanning modality by varying properties of the applied voltage such that there is a correlation in the sub-nanometer resolution between the applied voltage and the height within electrical double layer 115.

In certain embodiments, the scanning mechanism is adaptive as it compares the current measurement with the previously measured impedance at the prior frequency or phase step. In particular embodiments, from this comparison an algorithm can be applied to interpret if there is a variation or change to the measured signal which is two standard deviations from the previous measurement. In exemplary embodiments, the step size can first change linearly if the variation to the measured signal is within the two standard deviation threshold; then scanning of frequency or phase can take place logarithmically to the next decade where the scanning can then resume linearly.

Figure 5:
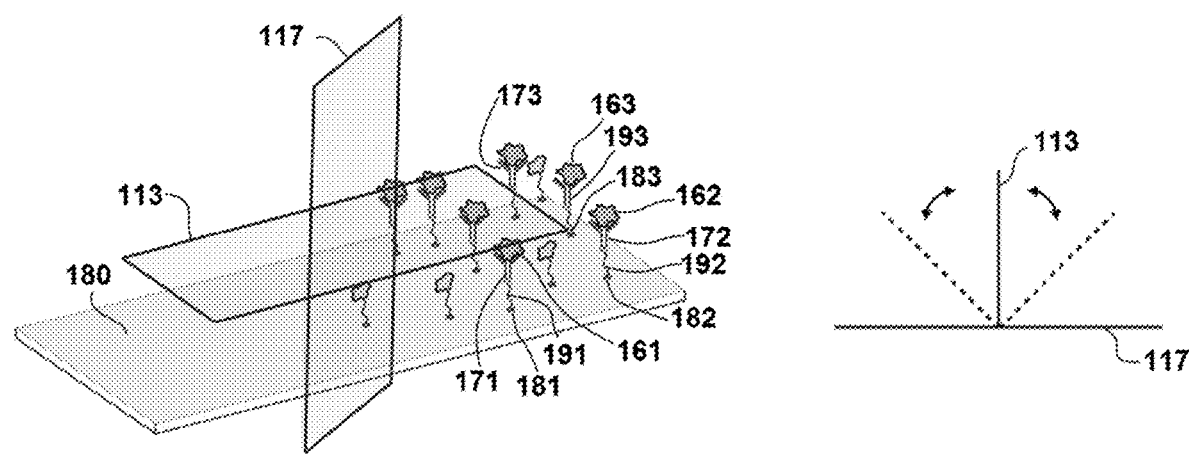
FIG. 5 A schematic representation of electrodes configured as analyte sensors on a substrate surface.

Referring now to FIG. 5, first, second and third electrodes 108, 106 and 110 can be configured as multiple sensors 181, 182 and 183 on a substrate surface 180. For purposes of clarity, not all sensors on surface 180 are labeled, and individual electrodes are not labeled in the sensors. It is understood that the electrode configurations for each sensor may comprise one of the configurations provided in this disclosure. Bi-functional linkers 191, 192 and 193 (including for example, a dithiobis succinimidyl propriante linker) can be coupled to sensors 181, 182 and 183 as shown in FIG. 5. A target-specific antibody 171, 172 and 173 can be coupled to bi-functional linkers 191, 192 and 193 configured to capture biomolecules 161, 162 and 163. In certain embodiments, each sensor may comprise a bi-functional linker and target-specific antibody configured to detect a different biomolecule so that multiple unique biomolecules can be detected by a plurality of sensors on surface 180.

During operation, a first electric field (represented by plane 113) is applied at a first phase angle to first and second electrodes 108 and 106 for one or more of sensors 181, 182 and 183. In addition, a second electric field (represented by plane 117) is applied at a second phase angle to second and third electrodes 106 and 110. In exemplary embodiments, the phase angle of electric fields 113 and 117 can be modulated. With both electric fields 113 and 117 being applied to second electrode 106, the phase angle between the electric fields 113 and 117 is constant (e.g., the fields are locked in phase and separated by a constant delta phase angle). In the embodiment shown, electric field 113 is applied parallel to substrate surface 180. In exemplary embodiments, parameters of electric field 113 (e.g., the frequency) can be modulated to change the distance between surface 180 and electric field 113 to detect ionic interactions between a biomolecule 185 and surface 180. Accordingly, the applied electric fields can be modulated to probe the ionic interactions in the Z-direction (perpendicular to surface 180) by changing the frequency, as well as they X-Y directions (parallel to surface 180) by changing the phase angle.

The modulus and imaginary components of the measured impedance of electric field 113 can be analyzed with the change in parameters. Distinctive markers of biomolecule 185 can be identified based on the changes in modulus and imaginary components of the measured impedance. As explained further below for example, a known biomolecule can be applied to surface 180 and the modulus and imaginary components measured with applied input parameter modulation to establish a standard calibration curve with different calibration response profiles for different biomolecules. In addition, the phase angle of applied electric fields 113 and 117 can be varied, and the rotational angle and phase current response analyzed to determine distinctive markers of biomolecules. Again, a known biomolecule can be applied to surface 180 and the rotational and phase current response measured with phase angle modulation to establish a standard calibration curve with different response profiles for different biomolecules.

The establishment of calibration response profiles can be prepared in various manners. In one embodiment, a linker is deposited on the substrate, the substrate is saturated with a moiety specific for the target analyte, e.g., a target specific antibody, a blocking buffer is applied to the receptor moiety saturated conformal circuit surface to minimize nonspecific binding or adsorption of other competing molecules onto the sensor surface, a buffer wash is performed, and the target analyte, e.g., antigen, is dosed onto the circuit. In designing the calibration curve for a target molecule, such as an antigen, increasing doses of the antigen are applied onto the conformal circuit and impedance measurements are obtained until steady state is reached. An increasing change to the measured impedance is expected with increasing dose of the target molecule such as an antigen. Once the calibration curve has been designed, an unknown dose of a test target molecule such as an antigen can be tested onto the antibody/receptor moiety saturated sensor surface, and the change in impedance is then evaluated against the calibration curve to determine the dose of the test target molecule.

In exemplary embodiments, the assignment to the native or unbiased surface is first performed where the buffer helps identify the effective impedance of the system. This impedance can help determine the signal threshold of the assay, and this number can change as a function of the buffer and the contact impedance of the electrode. Impedance matching between this measured baseline and the baseline of the potentiostat can be performed, and the conformal electrode can help to elongate electrical double layer 115 to enable the adaptive probing. The inherent surface charge, height, isoelectric behavior, flexibility (e.g., steric/conformational) of the capture probe can enable the assignment of the baseline measurement.

Figure 7:
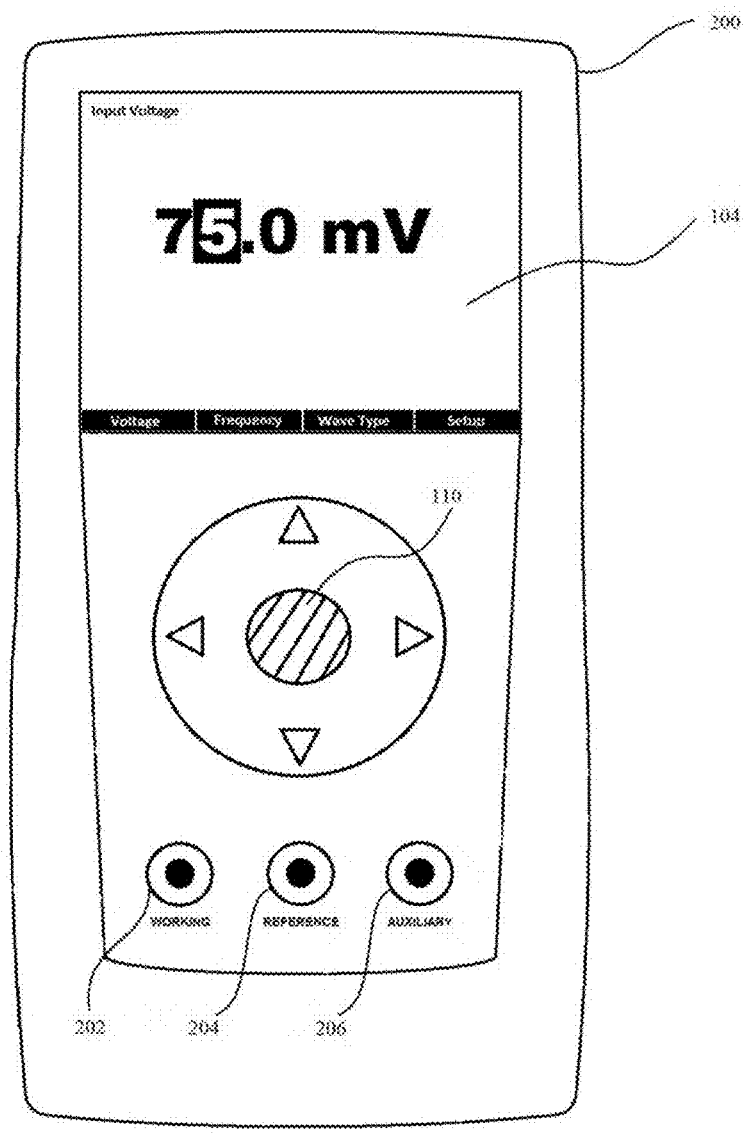
FIG. 7 Handheld potentiostat device.

A diagram depicting an example of one configuration of handheld potentiostat is found at FIG. 7. The handheld potentiostat 200 comprises an LCD display 104. The LCD display 104 provides a user interface that displays input and output data. For example, the LCD display may show an input voltage, an input frequency, a wave type, a target analyte name, a molecular concentration, an impedance, and a phase angle. The handheld potentiostat 200 may also comprise a mini-joystick 124, which enables the user to provide input to the handheld potentiostat 200. For example, the mini-joystick 124 may be used to navigate menus on the LCD display 104 and increase or decrease input voltage and frequency values. In some embodiments, the handheld potentiostat 200 may comprise buttons or a keypad in addition to or instead of a mini-joystick 124. The handheld potentiostat further comprises a first electrode port 202, a second electrode port 204, and a third electrode port 206. The electrode ports 202, 204, and 206 are used to connect wire leads to the first, second, and third electrodes.

Figure 6:
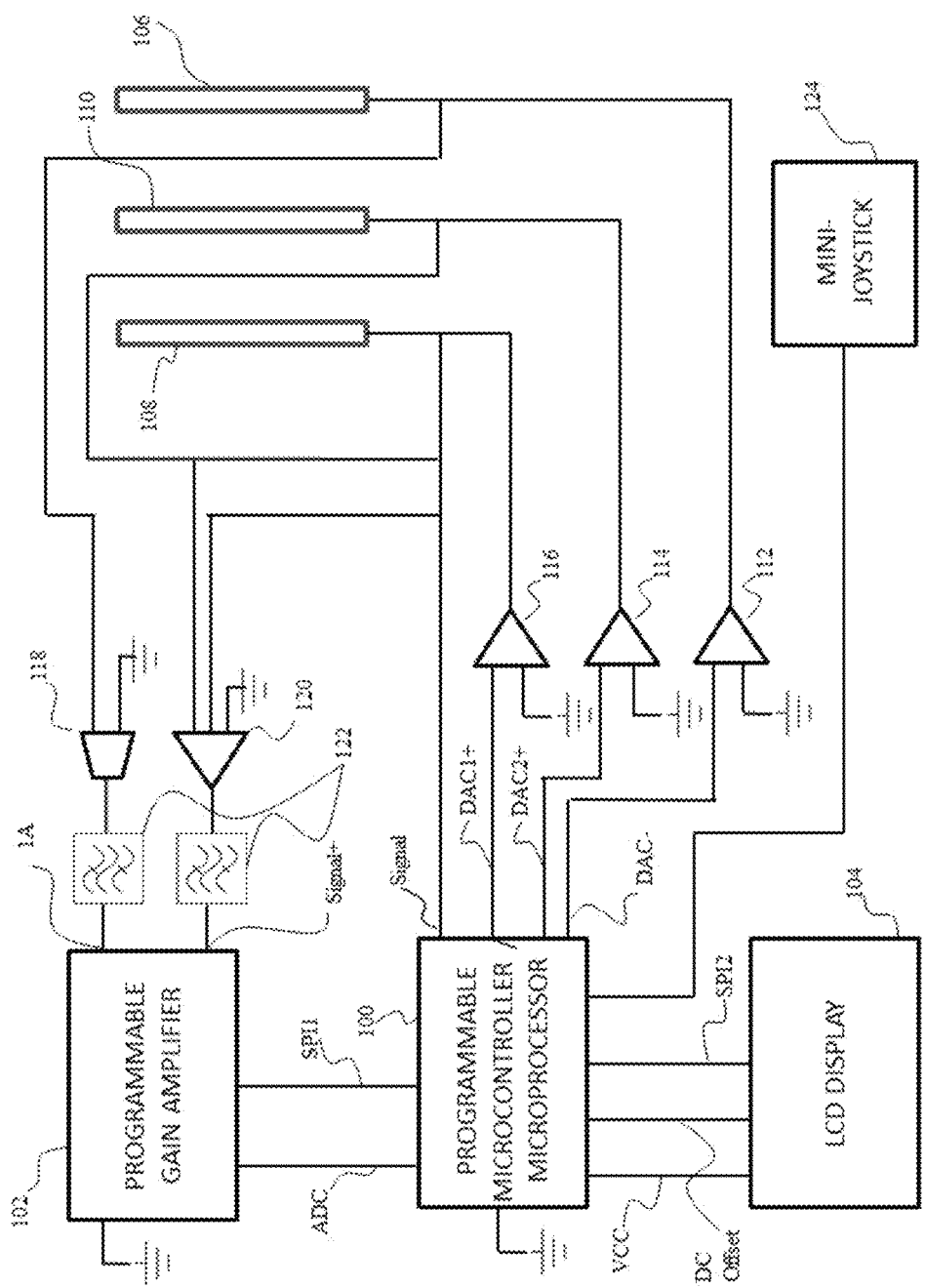
FIG. 6 A schematic representation of a representative three electrode handheld potentiostat.

A block diagram representing one possible potentiostat/electrode configuration is found at FIG. 6. The heart of operation for the potentiostat is carried out in the programmable microcontroller/microprocessor 100. The first operation of the microcontroller is providing user interface support through an LCD display 104. The serial peripheral interface SPI2 is used to communicate information processed in the microcontroller 100 to the LCD display 104. The microcontroller 100 uses VCC and DC Offset to supply power to the LCD display 104.

User input/response to options displayed on the LCD display 104 is received as analog signals through an analog-analog communication between the mini-joystick 124 and microcontroller 100. Using the mini-joystick 124, the user may select the electrical signal parameters, e.g., voltage, frequency, wave type, to be applied to the first electrode 108, second electrode 106, and third electrode 110. Alternatively, the mini-joystick 124 is used to select the type of molecule to be detected. After the test concludes, the LCD display 104 may display the names of analytes detected, the numerical concentration of the molecule(s) in the tested sample, impedances, and orientation angles.

Next, the microcontroller 100 is programmed to perform impedance spectroscopy characterization on the attached electrochemical sensor. Based upon the electrical signal parameters or molecule selected by the user, the programmable microcontroller 100 generates an first AC voltage on lines DAC1+ and DAC− that is applied to the first electrode 108 and second electrode 106, respectively, and a second AC voltage on lines DAC2+ and DAC− that is applied to third electrode 110 and second electrode 106, respectively. The AC voltages may be amplified by amplifiers 112, 114, and 116. In some embodiments, the resulting voltages of the first electrode 108 and third electrode 110 may fed back to the microcontroller 100 on the Signal line. The resulting voltage may differ from the applied voltage due to chemical reactions in the tested solution. The microcontroller 100 digitizes the voltage value of the second electrode 106, and the digitized voltage is used by the microcontroller 100 to adjust the applied AC voltage levels on lines DAC1+, DAC2+, and DAC−. In some embodiments, the voltages of the first electrode 108 and third electrode 110 may fed back to the programmable gain amplifier 102 on the Signal+ line. The programmable gain amplifier may digitize the voltage value of the second electrode 106 and send the digitized voltage to the microcontroller 100 over line SPI1, and the digitized voltage is used by the microcontroller 100 to adjust the AC voltage level on lines DAC+ and DAC−.

After two AC voltages are applied and a sample of an electrically conductive solution contacts the sensor, an AC current flows from the first electrode 108 through the second electrode 106 and from third electrode 110 through the second electrode 106. The amount of current flowing through the second electrode 106 depends upon the voltages applied to the second electrode 106, first electrode 108, third electrode 100, the binding of molecules on the electrodes, and the solution used. A programmable gain amplifier 102 measures the current flowing through the second electrode 106. Specifically, the transconductance amplifier 118 feeds a current to the programmable gain amplifier on line 1A. The current may be filtered by a bandpass filter 122. The bandpass filter 122 is automatically adjusted to permit signals at the applied frequency while rejecting noise at other frequencies. The programmable gain amplifier 102 then generates an amplified voltage from the current that is fed into the programmable microcontroller on line ADC. The amplification is necessary as the microcontroller operation thresholds are much greater than the small voltages and currents generated in this impedance spectroscopy application. In some embodiments, the amplified voltage on line ADC ranges between 20 mV and 6 V. If the amplified voltage on line ADC is too high or too low, the microcontroller 100 sends a signal to the programmable gain amplifier 102 over line SPI1 to increase or decrease the gain. In some embodiments, the binary gain of the programmable gain amplifier 102 may be adjusted between 1 and 128. In some embodiments, the scope gain of the programmable gain amplifier 102 may be adjusted between 1 and 200. The Signal+ line provides a reference voltage to the programmable gain amplifier 102 to calculate gain. The Signal+ voltage may be amplified by amplifier 120 and filtered by a bandpass filter 122.

The microcontroller 100 converts the analog amplified voltage to a digital signal. The microcontroller 100 then compares the digitized amplified voltage, which represents the amount of current flowing from the first electrode 108 and third electrode 110 through the second electrode 106, to the voltages applied to the first electrode 108 and second electrode 106 and to third electrode 110 and second electrode 106 to determine the impedance of the solution being tested. The microcontroller 100 performs arithmetic operations to calculate phase and amplitude changes in the amplified voltage with respect to the applied voltage as a function of frequency. Impedance is calculated using the following formula:

$$Z = \frac{V_m \sin \omega t}{I_m \sin(\omega t + \varphi)}$$

where $V_m$ represents the amplitude of the applied voltage, $I_m$ represents the amplitude of the resulting current flowing between the electrodes, $\omega$ is the angular frequency of the applied voltage and resulting current, and $\varphi$ is the difference in phase between the applied voltage and resulting current. Phase changes are calculated using the following formula:

$$\Phi = \frac{\Delta \varphi(v)}{\Delta \varphi(i)}$$

which is the ratio of the phase components of the input voltage to the phase components of the output current. In some embodiments, the microcontroller 100 uses a fast Fourier transform to determine the phase and amplitude changes as a function of frequency. In some embodiments, the microcontroller 100 uses a Laplace transform to determine the phase and amplitude changes as a function of frequency. In some embodiments, the microcontroller 100 performs multi-slice splitting and signal analysis to determine at which frequencies the change in impedance is the greatest. This estimation helps in characterizing the bio-electrochemical reactions occurring on the surface of the electrodes. The microcontroller 100 uses the change in amplitude and phase to calculate the concentration of the molecule in the sample.

The disclosed potentiostat may also vary the angular orientation of the second-third electrode's electric field with respect to the orientation of the first-second electrode's electric field. By default, if the third electrode is disposed parallel to the first and second electrodes, the electric field of the second-third electrodes is oriented perpendicular to the electric field of the first-second electrodes. On the other hand, if the third electrode is disposed perpendicular to the first and second electrodes, the electric field of the second-third electrodes is oriented parallel to the electric field of the first-second electrodes. During testing, the potentiostat varies the orientation of the electric field of the second-third electrodes and measures the current response at the third electrode. The electric field used in this process is given by the following equation:

$$\vec{E} = Em \sin(\omega t + \varnothing) X \Psi_\phi$$

where Em is the magnitude of the electric field, $\omega$ is the angular frequency, t is time, $\Phi$ is phase, X represents the cross product of the vectors, and $\Psi_\Phi$ is the angular orientation of the electric field. $\Psi_\Phi$ is a unity constant for the first-second electrodes' electric field. When the first, second, third electrodes are all planar, $\Psi_\Phi$ is 90 degrees+θ for the third-second electric field, where θ is a variable that rotates the electric field from 0 to 360 degrees. When the third electrode is perpendicular to the first and second electrodes, $\Psi_\Phi$ is 0 degrees+θ for the second-third electric field, where θ is a variable that rotates the electric field from 0 to 360 degrees. While θ is varied, the system measures the current response at the third electrode. The angular orientation of the electric field versus the current response is unique for each target analyte, and is used by the system to detect the presence of target analytes.

Before being used to measure unknown quantities of a target analyte, the handheld potentiostat must be calibrated. Calibration is performed by measuring the impedance of solutions containing known quantities of a target analyte. Specifically, the user may perform impedance measurements of preferably four different solutions containing four different concentrations of the target analyte. For each calibration test, the user inputs the target analyte concentration into the handheld potentiostat using the mini-joystick. The handheld potentiostat records the impedance for each test. After the tests are completed, the system completes the calibration by determining the coefficients in the following equation, $$z_i = b_n x^n + b_{n-1} x^{n-1} + \ldots + b_1 x + c$$

where $z_i$ is the measured impedance, x is the known concentration of the target analyte, and $b_n$, $b_{n-1}$, $b_1$, and c are the coefficients. The order of the polynomial, n, may be between two and five, and preferably two. The handheld potentiostat determines the unknown values of the coefficients using linear regression and least squares analysis.

In some embodiments, the microcontroller 100 is an Intel® microcontroller. In other embodiments, the microcontroller 100 is an Intel® microprocessor. In other embodiments, the microcontroller 100 is an ARM Cortex™-M microcontroller. In other embodiments, the microcontroller 100 is an ARM Cortex™ microprocessor.

In particular embodiments, the microcontroller 100 applies an AC voltage between 5 mV and 500 mV to first electrode 108 and second electrode 106 and to third electrode 110 and second electrode 106. The microcontroller applies an AC voltage whose frequency ranges between 50 Hz and 1,000 Hz to the electrodes. When a varying voltage is applied, a capacitive double layer is formed in the solution. As the frequency of the applied voltage increases, the distance of the capacitive layer from the electrodes increases. In some embodiments, the user selects a minimum and a maximum frequency, and the microcontroller 100 applies voltages having frequencies ranging between the selected minimum and maximum frequencies.

In some embodiments, the handheld potentiostats disclosed herein perform impedance spectroscopy analysis on a biosensing platform. Very low voltage is necessary for the use of these potentiostats in order to be applicable for biosensing, as proteins and biomolecules are sensitive. In some embodiments, the range of appropriate voltage may be may be 50 mV to 500 mV, but the appropriate voltage will depend on the application. In applications to protein based sensing, the voltages will be in the range of 5 mV to 20 mV. In application to cells and DNA, the voltage ranges will be between 100 mV to 2V. Similarly, due to the application of very small voltages, the current response is in a similar range or much lower, as there is loss due to bulk solution medium. In some embodiments, the range of appropriate current is 10 pA to 10 mA and, as with the voltage, the appropriate current response will depend on the application. In applications to protein based sensing, the current response will be in the range of 10 pA to 100 nA. In application to cells and DNA, the current response will be between 100 nA to 10 mA.

The disclosed potentiostats may be used at fixed or variable frequencies. Based on the application, the fixed and variable frequency ranges will vary. For most biosensing applications, the range of frequencies used is between 50 Hz and 100 kHz. Upon optimization of the electrical debye length changes corresponding to a protein of interest, the fixed frequency can be estimated. Detection at the respective frequency can improve detection speeds and reduce non-specific signals.

In addition to performing impedance spectroscopy, the handheld potentiostats disclosed herein can be used as a source meter and also as a voltammetry tool through easy-to-choose options on the LCD display.

The handheld potentiostats disclosed herein are easily portable and have a hand friendly form factor. It may be about or at least 1, 2, 3, 4, 5, 6, 7, 8, 9, or 10 inches by about or at least 1, 2, 3, 4, 5, 6, 7, 8, 9, or 10 inches. It is specifically contemplated that it may be about 5 inches by about 3 inches. It is also specifically contemplated that the entire device, including the programmable gain amplifier, the programmable microcontroller, and the LCD display for output that are indicated on the diagram, be within these sizes.

Figure 8:
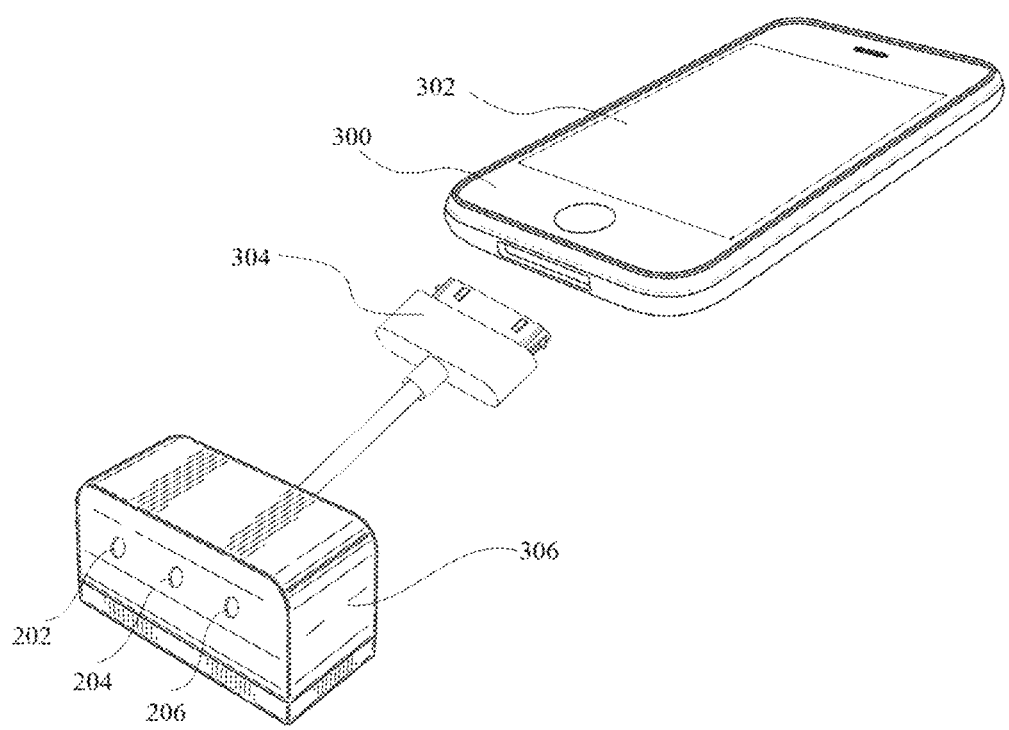
FIG. 8 A smartphone embodiment of a handheld potentiostat.

A diagram depicting a smartphone embodiment of the handheld potentiostat is found at FIG. 8. The handheld potentiostat comprises a smartphone 300 and a potentiostat adaptor 306. The smartphone is operably coupled to a potentiostat adaptor 306 using a cable 304, preferably a Micro USB or a proprietary connector. The cable 304 provides bi-directional communication between the smartphone 300 and the potentiostat adaptor 306. The potentiostat adaptor comprises a first electrode port 202, a second electrode port 204, a third electrode port 206, a microcontroller 100, and a programmable gain amplifier 102. Users install a custom potentiostat software application onto the smartphone 300 that provides user input and output and microcontroller communication functionality. Users may provide input to the smartphone 300, including the input voltage, input frequency, and wave type, using a touchscreen 302. In other embodiments, users provide input to the smartphone using a keypad. The smartphone 300 displays output, such as the concentration of the target analyte on the smartphone's touchscreen 302.

The potentiostats disclosed herein also perform with low noise threshold at the desired range of operation for biosensing. Currently, potentiostats are designed with electrochemical applications in mind. The integrated circuits used for these applications have reasonable noise thresholds. When applying to biosensing, the measured signals of the available devices are in many cases within the noise threshold, thus rendering majority of the available potentiostats unsuitable.

The potentiostats disclosed herein are also programmable to perform three electrode impedance spectroscopy using fast Fourier transforms and Laplace transforms. Existing potentiostats use Lissajous curves methods to estimate phase change in the measured current response. Though this has been perfected for applications involving high voltages and currents, it is not optimized for analysis of voltage and current responses as necessary for biosensing. Fast Fourier transform-based and Laplace transfer-based estimation, which is more appropriate for these applications, has not been widely used due to complexity in implementation as it demands high processor speeds. Using fast Fourier and Laplace transforms assists in digital signal analysis by reducing noise and preserving signal integrity; both of which are critical for biosensing.

The potentiostat's calculations using fast Fourier transforms is described below. The microcontroller applies a sinusoidal voltage of the form $V(t) = v \sin(\omega t)$, where v is the amplitude of the signal and w is the angular frequency. In preferred embodiments, the microcontroller applies sinusoidal voltages at varying frequencies. The microcontroller measures the resulting current signal, which is of the form $I(t) = i \sin(\omega t + \varphi)$, where i is the amplitude of the signal and $\varphi$ is the phase shift of the signal. The microcontroller converts the applied voltage signal from the time domain into the frequency domain by applying a fast Fourier transform, $$V(\omega) = \sum_{n=0}^{N/2-1} v(t)_n^{even} e^{-2\pi j n k / (\frac{N}{2})} + e^{-2\pi j k / N} \sum_{n=0}^{\frac{N}{2}-1} v(t)_n^{odd} e^{-2\pi j n k / (\frac{N}{2})}.$$

Likewise, the microcontroller converts the resulting current signal from the time domain into the frequency domain in step 506 by applying a fast Fourier transform, $$I(\omega) = \sum_{n=0}^{N/2-1} i(t)_n^{even} e^{-2\pi jnk/(\frac{N}{2})} + e^{-2\pi jk/N} \sum_{n=0}^{\frac{N}{2}-1} i(t)_n^{odd} e^{-2\pi jnk/(\frac{N}{2})}.$$

The resulting current frequency signal is verified with the applied voltage signal and noise occurring at other frequencies is filtered out. The microcontroller determines the frequency at which the maximum impedance change occurred using multi-slice splitting, wherein the applied frequency spectrum is sliced into individual discrete frequency points. The microcontroller then compares the frequency at which the maximum impedance change occurred to the reference frequency point stored in memory for the specific analyte being tested. The microcontroller estimates the concentration of the tested analyte by applying the same equation used in calibration, $z_i = b_n x^n + b_{n-1} x^{n-1} + \ldots + b_1 x + c$, where $z_i$ is the impedance at the frequency at which the maximum impedance change occurred, and $b_n$, $b_{n-1}$, $b_1$, and c are coefficients calculated during calibration, and x is the target analyte concentration being computed. In preferred embodiments, the equation is quadratic.

Figure 12:
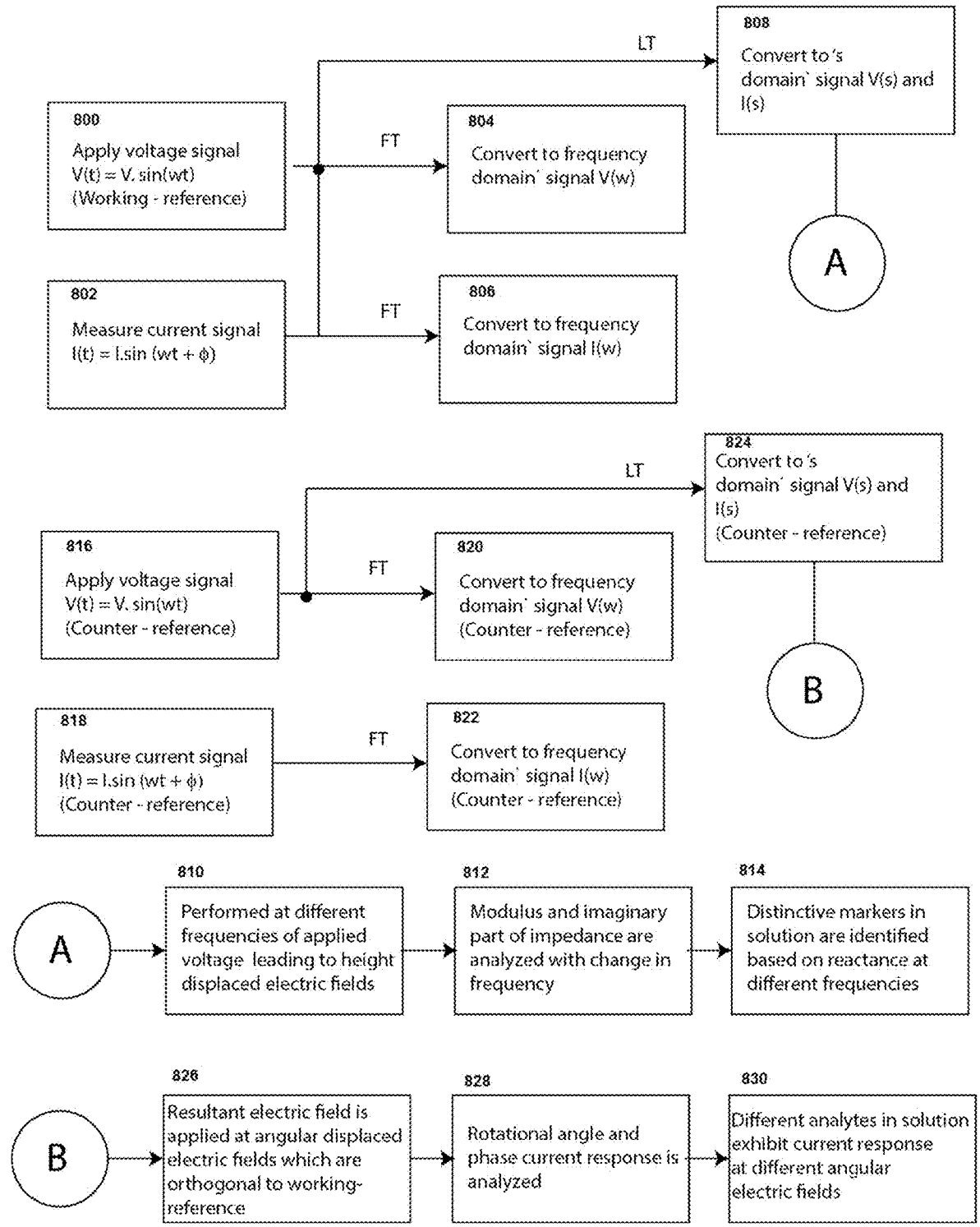
FIG. 12 A flowchart illustrating the operation of the potentiostat.

FIG. 12 is a flowchart illustrating the operation of one embodiment of the potentiostat. At step 800, a sinusoidal voltage is applied between the first and second electrodes. At step 802, the system measures the resulting current flowing between the first and second electrodes. At steps 804 and 806, the voltage and current are converted into frequency domain signals using a fast Fourier transform. In step 808, the voltage and current are converted into s domain signals using a Laplace transform. In step 810, the sinusoidal voltage applied to the first and second electrodes is applied at different frequencies, which results in the capacitive double layer being formed at different distances from the electrodes. In step 812, the modulus and imaginary part of the impedance are analyzed with the change in applied signal frequency. At step 814, distinctive markers in the solution are identified based upon the measured reactance at different frequencies. At step 816, the system applies a sinusoidal voltage between the third and second electrodes. At step 818, the system measures the resulting current flowing between the third and second electrodes. At steps 820 and 822, the system applies a fast Fourier transform to convert the applied voltage and resulting current signals into the frequency domain. In step 824, the signals are converted into the s domain using a Laplace transform. In step 826, the resultant electric field is applied at varying angles which are orthogonal to the first-second electrode. At step 828, the rotational angle and current response is analyzed. At step 830, the system determines the presence of one or more analytes in solution based upon the current response exhibited at different angular electric fields.

The potentiostats disclosed herein also contain cost-effective components, manufacturing involves very simple surface mount device assembly, and the disclosed devices have low-thermal noise due to use of modern current amplifiers and programmable gate arrays.

Finally, the potentiostats disclosed herein have applicability as a source meter, a voltammetry tool, and for standard current measurements. The potentiostats can be customized for the different applications by making modifications to the program that run the operations and produce results. The programmable gain amplifiers have a broad range of operation (mV-V/pA-mA) and hence can be used for different voltammetry applications to biosensing as well as general applications. Microprocessors/microcontrollers offer extensive programming liberties and hence application of the potentiostats to different operations will require only software changes and not hardware.

The potentiostats disclosed herein are highly adaptable and generates results rapidly. For a single channel assay, when a single channel EIM detection scheme and a 32-bit microcontroller (40-10 kHz) is used, it results in a read time of less than 40 seconds.

B. Substrates and Conductive Materials

The substrates contemplated include porous nanotextured substrates. In some embodiments, paper, nitrocellulose, fabric, leaves, bark, or shells is contemplated; however, any porous, hydrophilic substrate that wicks fluids by capillary action can be used as the substrate in the methods and devices described herein. Non-limiting examples include cellulose and cellulose acetate, paper (e.g., filter paper and chromatography paper), cloth or fabric, porous polymer film, porous plastic, or leaves. In some embodiments, the substrate is biodegradable. Preferably, the substrate is paper.

The porosity of the substrate in conjunction with conductive ink screen printing can be leveraged to pattern conformal circuits. Any size and thickness of substrate may be used. The dimensions of the substrate are not key to functionality of the circuit. The critical parameter that impacts the performance of the circuit is the porosity of the substrate. Porosity can vary from $10 \times 10^7$ to $10 \times 10^{18}$ pores/mm$^2$ and the substrate, including its porosity, is selected based on the size of the target analyte. This porosity can be adjusted or tuned using a variety of techniques, e.g., coatings or treatments. Examples of possible treatments and coatings include wet treatments such as acidic or alkaline etching, use of layer by layer deposition of self-assembled monolayers, and dry treatments such as reactive ion etching and plasma etching.

The substrate can be up to 100 microns thick, and there are no capping factors on the lateral dimensions. In some embodiments, the substrate may be 1, 2, 3, 4, 5, 6, 7, 8, 9, or 10 cm by 1, 2, 3, 4, 5, 6, 7, 8, 9, or 10 cm, or any size in between. In particular embodiments, the substrate is 1 cm by 1 cm.

It is contemplated that any appropriate conductive material may be used, and a range of conductive inks are contemplated. Conductive inks usually contain conductive materials such as powdered or flaked silver and carbon like materials. In some embodiments, the conductive ink is carbon, silver, or metal or metal oxide nanoparticle-infused carbon inks. In some embodiments, the metal or metal-oxide nanoparticle-infused carbon ink is 1% by volume infused with a noble metal or metal oxide. In certain examples, the carbon ink is infused with gold, platinum, tantalum, silver, copper, tin, indium-tin oxide, grapheme, grapheme oxide, zinc oxide, titanium oxide, iron oxide, or molybdenum oxide. The use of additives such as metal or metal oxide nanoparticles to carbon ink changes the conductive carbon ink into semi-conducting ink. In some embodiments, this semi-conducting ink pattern may be used for designing the diode and transistor behavior. In some embodiments, native conducting ink may be used for obtaining the impedance changes. The ink substrate (i.e., the combination of the ink and the substrate) is the base electrode surface over which the biomolecule chemistry is implemented for achieving molecular diagnostics.

The nature of the ink is dependent on the type of sensing and analysis desired. In some embodiments, when passive sensing with an electrical reader is necessary, the ink is only conducting. More particularly, for passive devices, conductive/semi-conducting nanoparticles may be dispersed in a matrix, or the ink may contain metal nanoparticles, metal oxide nanoparticles, or electro active polymer matrices. In situations where active sensing, such as with a multimeter, is useful, the ink can be conducting and semi-conducting, or conducting stacks. Where optical sensing is appropriate, the ink may be photo catalytic. In situations where colorimetric sensing is useful, the ink will contain nanoparticles that agglomerate during sensing. Hybrid stacking of material can also give additional properties to the ink.

In some embodiments, the conformal circuit may include a redox material, such as derivatives of copper, potassium, magnesium, and rubidium. These materials bind with the receptor of the analyte immobilized onto the conformal circuit. During the binding of the analyte onto the receptor with the redox material there is an amplification in the number of charges routed through the conformal circuit due to the reduction or oxidation of the redox material. This process is distinct from the use of redox electrodes, where the redox material is immobilized onto the redox electrode itself. During the application of a bias potential or a current to the redox material on a redox electrode, this material either undergoes a reduction or oxidation, thus binding to the target analyte in this state and modifying the analyte that is being tested/evaluated.

C. Methods of Patterning

The conformal circuits are assembled by performing engineering to standard paper products. Porosity in paper is leveraged towards achieving control in circuit formation. A stencil of the circuit design is transferred onto the substrate surface in any appropriate manner. The parameters of the desired pattern are determined by the molecules to be detected. A person of skill in the art would recognize the appropriate transferring method in view of the desired pattern. For example, smaller patterns or smaller feature sizes require the more advanced printing techniques, e.g., masking and lithography. These processes are discussed in more detail below.

Stencils contain a pattern of holes or apertures through which conductive materials could be deposited onto the hydrophilic substrates. Alternatively, in an etching process, stencils contain a pattern of holes or apertures through which conductive materials could be etched to form a pattern of metal on the hydrophilic substrates. Stencils could be made from a variety of materials such as metal, plastic, or patterned layers of dry-film resist. Non-limiting examples of metals for manufacturing stencils include stainless steel and aluminum. Non-limiting examples of plastic for manufacturing stencils include mylar. Alternatively, patterned layers of dry-film resist can be used as stencils. In one or more embodiment, metals or plastics are used to manufacture stencils and patterns of metallic pathways can be designed on a computer using a layout editor, (e.g., Clewin, WieWeb Inc.) and stencils based on the design can be obtained from any supplier (e.g., Stencils Unlimited LLC (Lake Oswego, Oreg.)). In certain embodiments, the stencil can be removed from the paper after deposition. In certain other embodiments, one side of the stencil is sprayed with a layer of spray-adhesive (e.g., 3M Photomount, 3M Inc.) to temporarily affix the stencil to the paper substrate. After deposition, the stencil can be peeled away from the paper. The stencils can be reused multiple times, e.g., more than 10 times. In other embodiments, patterned layers of dry-film resist can be used as stencils. Dry film resist can be patterned when exposed to UV light through a transparency mask and developed in dilute sodium hydroxide solution. The patterned dry-film resist can be attached to a coating sheet of plastic or directly affixed to the hydrophilic substrates by pressing the resist-side to the surface of the hydrophilic substrates and passing multi-sheet structure through heated rollers in a portable laminator (Micro-Mark, Inc.). The coating sheet of plastic can then be peeled away, resulting in a sheet of paper with dry film resist patterned on one side.

A variety of deposition methods could be used to deposit electrically conductive materials onto the hydrophilic substrates of the microfluidic devices. Non-limiting examples of the deposition methods include depositing conductive materials using stencils, depositing conductive materials by drawing conductive pathways, depositing conductive materials by inkjet or laser printing, depositing conductive materials by attaching commercially available or homemade conductive material tapes onto the hydrophilic substrates, depositing conductive materials by drawing conductive pathways, or depositing conductive materials by introducing conductive fluids onto the hydrophilic substrates or the hydrophilic channels of the microfluidic devices. Alternatively, conductive materials could be embedded in the pulp or fibers for manufacturing the hydrophilic substrates to allow for manufacturing hydrophilic substrates containing conductive materials.

It is specifically contemplated that the circuit design may be transferred onto the substrate surface either through (a) dip coating (b) embossing or (c) masking and lithography. Dip coating and embossing allow for feature resolution in hundreds of microns, more particularly up to 100 nanometers/0.1 micron, and masking and lithography allows for feature resolution in 1-10 micron regime. These techniques are well known to those of skill in the art. See Reighard and Barendt, 2000. In particular embodiments, the circuit may be designed on a 3D printer and the design may be transferred to the substrate by embossing the circuit onto the substrate.

The lateral porosity of the substrate is leveraged to generate the conformal circuits disclosed herein. Vertical porosity is not suitable, and therefore a metal barrier of thickness in the order of 100s of nm achieves this goal. The thickness of deposited material also corresponds to the thickness of the substrate in some regions to change the electrical behavior of the substrate.

In a particular embodiment, the entire paper surface is dip coated. Biomolecules interacting with the conductive ink surfaces alone are responsible for the measured signal. There are no flow considerations to be taken into account. Hence, biomolecule interactions are primarily diffusion and capillary action driven and therefore larger the pores faster is the interaction. Multiple layers of dip coating have been adopted, where appropriate. This technique is most relevant when the intent is to design immunoassays requiring multiple layers of molecules incorporated onto the sensor platform.

D. Detection of Biomolecules

These conformal circuits can be applied for a wide range of molecular diagnostics and analysis, and therefore can be used on any sample that is suspected of containing a molecule of interest such as food, water, soil, air, bodily fluids such as blood serum, detergents, ionic buffer, etc. In some embodiments, the sample is any liquid sample or solid that can be solubilized or dispersed in a liquid. In other embodiments, the circuits can be used to detect toxins or other molecules in an air sample. For example, the circuit can be used to detect carbon monoxide, greenhouse gases such as $NO_x$, $SO_x$, $NH_4$, $O_3$, and other environmental toxins. The circuits can be used to design simple affinity based assays for mapping presence of enzymes and physiological ions. These can be used to develop assays to study antibody-antigen interactions and to determine presence or absence of a wide range of protein biomarkers expressed at ultra-sensitive concentrations. Genomic assays can also be developed using these circuits.

A single step immunoassay can be used in connection with the conformal circuits. In some embodiments, label free immunoassays using electrochemical sensors are appropriate (Vertergaard, et al., 2007). In a particular embodiment of protein diagnostics, a single primary antibody without a tag is used and, based on the base circuit, controlled and mapped modulations to the electrical circuit parameters are achieved during detection of the proteins. The system can be designed to detect quantitatively (e.g., an electrochemical impedance spectroscopy electronic reader).

The conformal circuits disclosed herein may be prepared for the immunoassay in any appropriate manner. In one embodiment, a linker is deposited on the substrate, the substrate is saturated with a moiety specific for the target analyte, e.g., a target specific antibody, a blocking buffer is applied to the receptor moiety saturated conformal circuit surface to minimize nonspecific binding or adsorption of other competing molecules onto the sensor surface, a buffer wash is performed, and the target analyte, e.g., antigen, is dosed onto the circuit. In designing the calibration curve for a target molecule, such as an antigen, increasing doses of the antigen are applied onto the conformal circuit and impedance measurements are obtained until steady state is reached. An increasing change to the measured impedance is expected with increasing dose of the target molecule such as an antigen. Once the calibration curve has been designed, an unknown dose of a test target molecule such as an antigen is tested onto the antibody/receptor moiety saturated sensor surface, and the change in impedance is then evaluated against the calibration curve to determine the dose of the test target molecule.

Analyte confinement is achieved within the nanoscale texture of the substrate, and the size-based confinement of the target analyte onto the substrate is achieved using conductive ink. Analytes interacting with the conductive ink in a single step immunoassay format perturb the (a) electrical double layer, (b) charges in the depletion layer in the diode, and (c) gate current characteristics of transistor resulting in the detection of the biomolecule of interest. As ultra-low volumes in the range of 1-10 micro liters are needed, the issue of controlled flow does not exist. Primarily spotting of the fluid on the substrate surface is sufficient to achieve associated interaction for biomolecule detection.

The conformal circuit and detection devices disclosed herein can be designed to detect either quantitatively (e.g., an EIS electronic reader) or qualitatively (e.g., color change). In addition, the system can be designed to detect a singlet (one analyte), multiplex (multiple analytes of same type), or multiplexicity (multiple analytes of different types).

The conformal circuits disclosed herein are highly versatile. For a single channel assay, a sample volume of less than 125 μL is needed, it has a dynamic range of detection of 1 pg/mL-10 μg/mL, and it can be useful for molecules at or between 1 and 100 nm. For multi-channel detection, a sample volume of less than 75 μL is needed, it has a dynamic range of detection of 1 pg/mL-10 μg/mL, there can be a minimum of 2 channels and a maximum of 8 channels, and it can be useful for molecules at or between 1 and 100 nm. For multiplexicity detection, a sample volume of less than 50 μL is needed, it has a dynamic range of detection of 1 pg/mL-10 μg/mL, there can be a minimum of 2 channels and a maximum of 16 channels, and it can be useful for molecules at or between 1 and 100 nm.

The potentiostats disclosed herein are highly adaptable and generates results rapidly. For a single channel assay, when a single channel EIM detection scheme and a 32-bit microcontroller (40-10 kHz) is used, it results in a read time of less than 40 seconds. For multi-channel detection, when a serial multi-channel EIM and a 16-bit/32-bit microcontroller (40-10 kHz) is used with a minimum of 2 channels and a maximum of 8 channels, results are generated in less than 40 seconds per channel. For multiplexicity detection, when a parallel multi-channel EIM and a 32-bit/64-bit microcontroller (40-10 kHz) is used with a minimum of 2 channels and a maximum of 16 channels, results are generated in less than 30 seconds per channel.

E. Kits

In some embodiments, contemplated are kits comprising conformal circuits and a potentiostat. In some embodiments, these kits are designed to accommodate a particular target analyte, e.g., a particular protein of interest. In one embodiment, the kit will comprise conformal circuits comprising a nanotextured porous substrate which is appropriate for the target analyte, which will have an appropriate pattern transferred to it, where the pattern is made up of an appropriate ink. In addition, the kit will further comprise a potentiostat which is calibrated to generate the data of interest to the user for the particular target analyte.

For example, a conformal circuit designed to detect C-reactive protein would have a substrate of nanoporous material, e.g., paper, having a porosity of $10^{13}$ to $10^{15}$ pores/cm$^2$ of 200 nm pores, where the circuit is made of a pattern that is interdigitated or edge-free interdigitated, or a concentric ring made using metal or metal-oxide nanoparticle-infused carbon ink infused with gold/platinum/silver/copper/nickel/indium tin oxide/iron oxide. The parameters of interest that would be inputted into the potentiostat include the applied voltage of 10 mV and an applied frequency and range of 20 to 10 KHz. Finally, the parameters of interest for analysis include the frequency of analysis, applied voltage, current measured, calculated impedance, estimated concentration, and standard calibration curve.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 9:
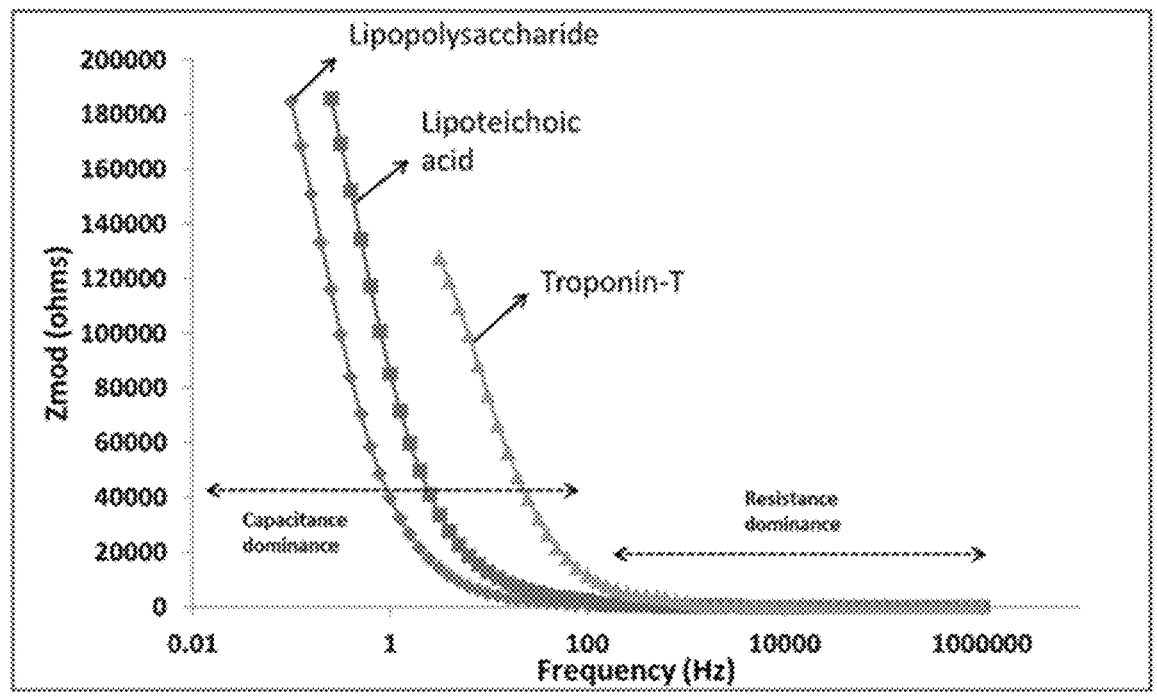
FIG. 9 A Bode plot illustrating impedance vs. frequency for different proteins.

FIG. 9 is a Bode plot representing the impedance modulus versus frequency of the applied signal for a solution containing lipopolysaccharide, lipoteichoic acid, and Troponin-T. FIG. 9 illustrates the frequency at which capacitance and resistance dominance is observed. The plot demonstrates the presence of distinct protein biomarkers in the solution, but does not quantify the protein biomarkers or their specificity in binding.

Figure 10:
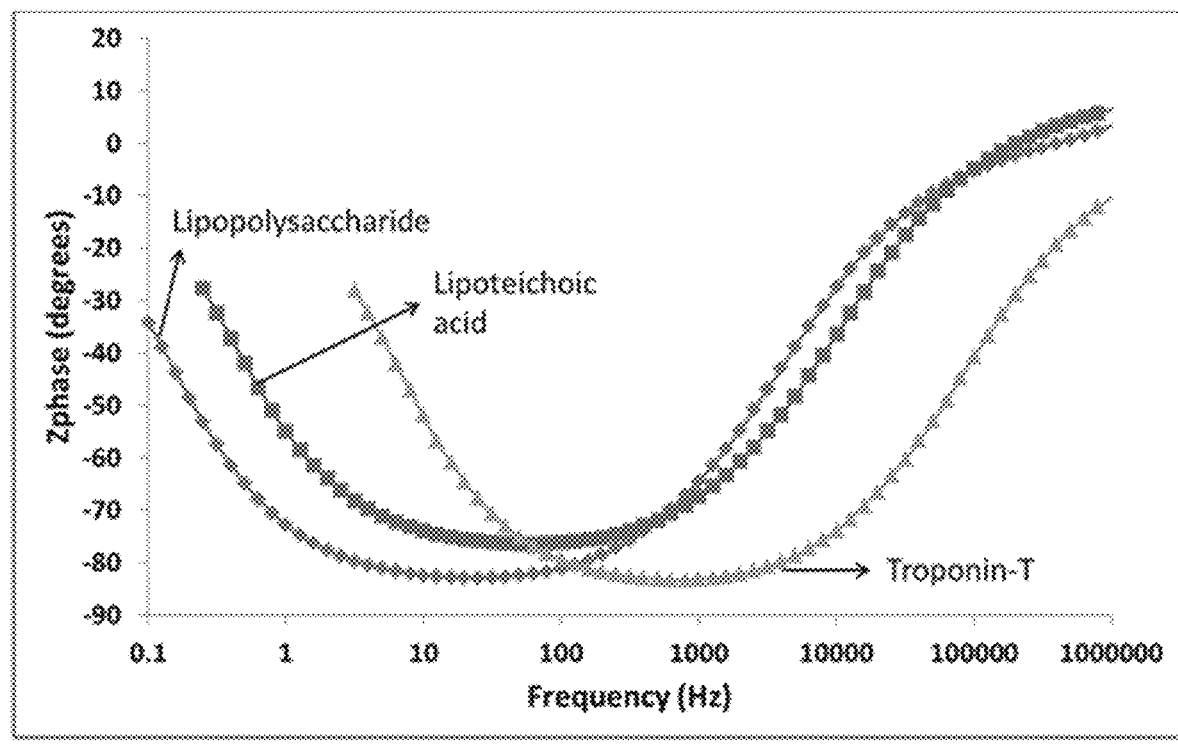
FIG. 10 A Bode plot illustrating impedance vs. frequency for different proteins.

FIG. 10 is another Bode plot representing phase change in the impedance versus the frequency of the applied signal for a solution containing lipopolysaccharide, lipoteichoic acid, and Troponin-T. The protein biomarkers exhibit unique impedance phase profiles that demonstrate the ability to distinguish multiple biomarkers in solution based upon spectroscopic analysis. The plot does not quantify the protein biomarkers or their specificity in binding.

Figure 11:
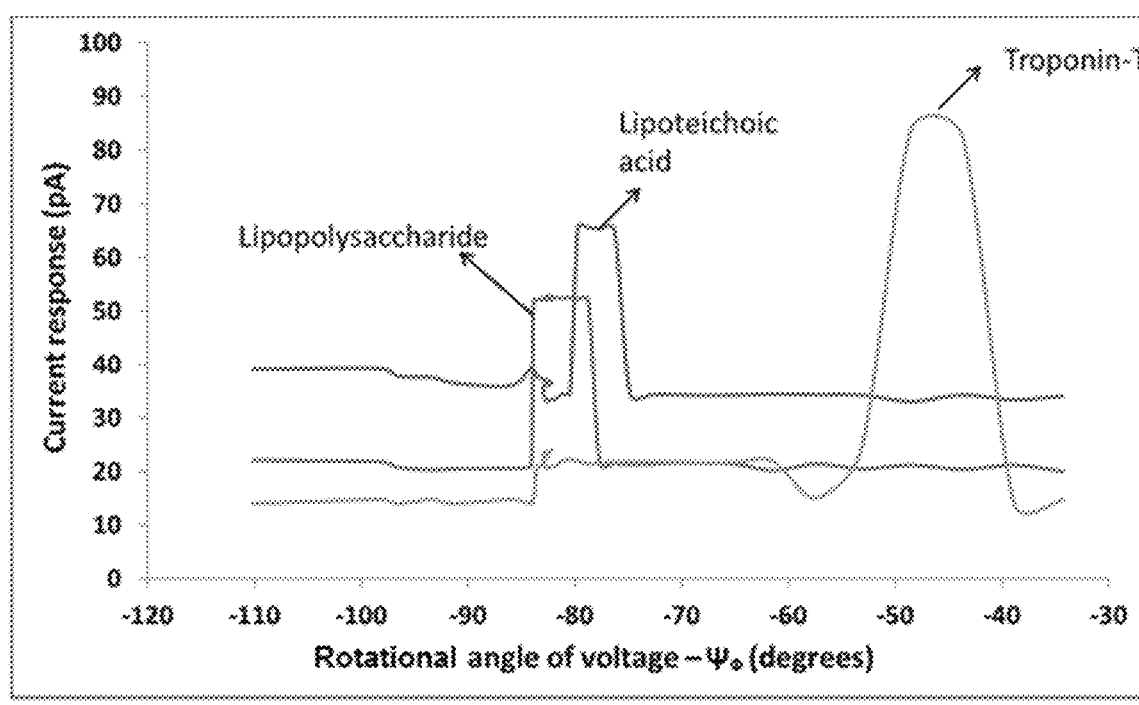
FIG. 11 A plot illustrating the current response vs. rotational angle for different proteins.

FIG. 11 is a plot of the angular orientation of the second-third electrode electric field versus the measured output current at the third electrode for a solution containing lipopolysaccharide, lipoteichoic acid, and Troponin-T. The protein biomarkers detected at the electrode-solution interface demonstrate unique phase response properties under the influence of orthogonally intersecting electric fields. The three protein biomarkers tested demonstrate unique current responses at varied orientation angles of applied electric fields.

FIG. 13 is a table listing various species of target analytes system and associated system configurations.

G. Experimental Data

FIG. 14 is a graph of a change in impedance (measured in ohms) versus concentration of lipopolysaccharide (measured in fg/mL) as detected by an exemplary embodiment of the present disclosure.

Figure 15:
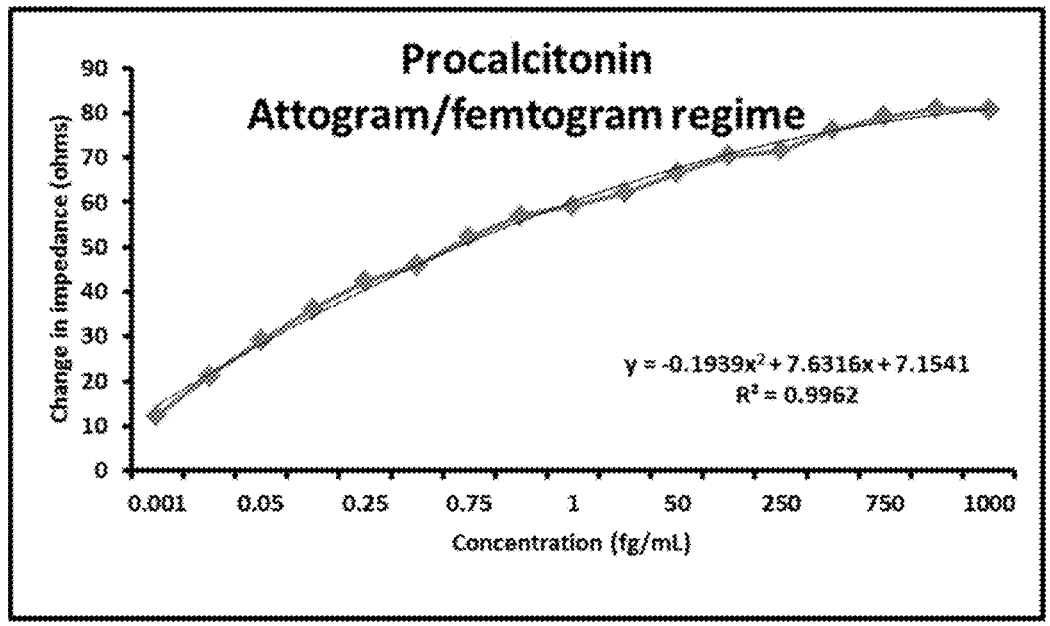
FIG. 15 A graph of a change in impedance versus concentration of procalcitonin.

FIG. 15 is a graph of a change in impedance (measured in ohms) versus concentration of procalcitonin (measured in fg/mL) as detected by an exemplary embodiment of the present disclosure.

Figure 16:
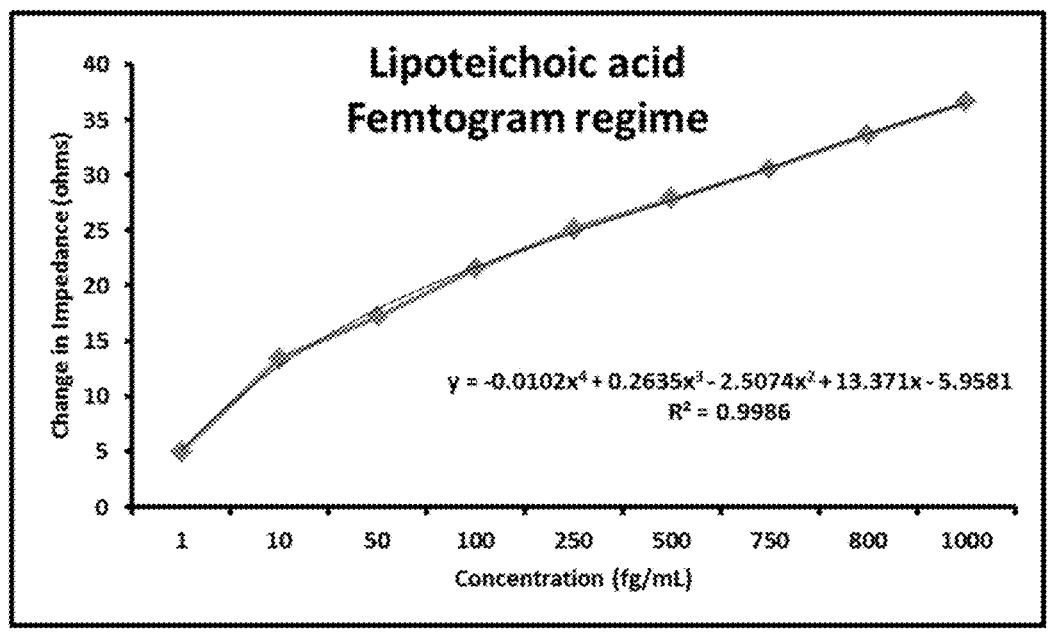
FIG. 16 A graph of a change in impedance versus concentration of lipoteichoic acid.

FIG. 16 is a graph of a change in impedance (measured in ohms) versus concentration of lipoteichoic acid as (measured in fg/mL) detected by an exemplary embodiment of the present disclosure. The linear range of operation for the detection of lipopolysaccharide, procalcitonin, and lipoteichoic acid was 1 fg/mL-1 µg/mL.

Additional data was collected regarding the detection of miRNA 21. The detection of small RNA molecules to study regulation of target gene expression has shown value. For example, miRNA's are key players in cancer regulation. In one test, the number of copies of miRNA 21 in a cell lysate solution was detected. The test sample included miRNA 21 enriched cells. A 20 bp oligo nucleotide on a paper cartridge targeted miRNA 21, and the control was wilde-type cells. A high relative concentration of miRNA 21 (e.g. greater than 200 copies/cell) was detected.

Figure 17:
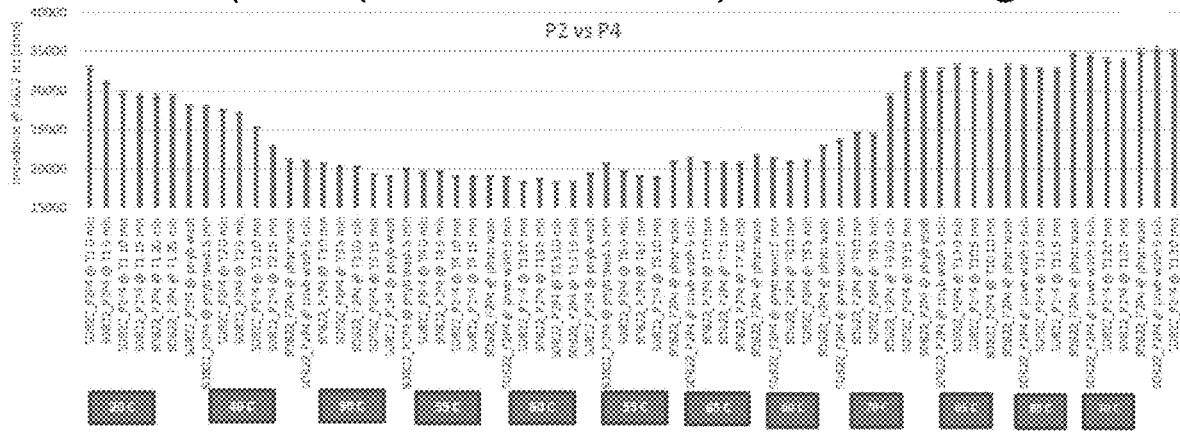
FIG. 17 A graph of measured impedance regarding the detection of miRNA sequence (P4) with a specific capture probe (P2) at various temperatures and times.

Additional data was collected regarding the detection of miRNA sequence (P4) with a specific capture probe (P2). FIG. 17 represents the measured impedance (in ohms) at various temperatures and times. The impedance at the capture probe was 32.452 kohms.

Figure 18:
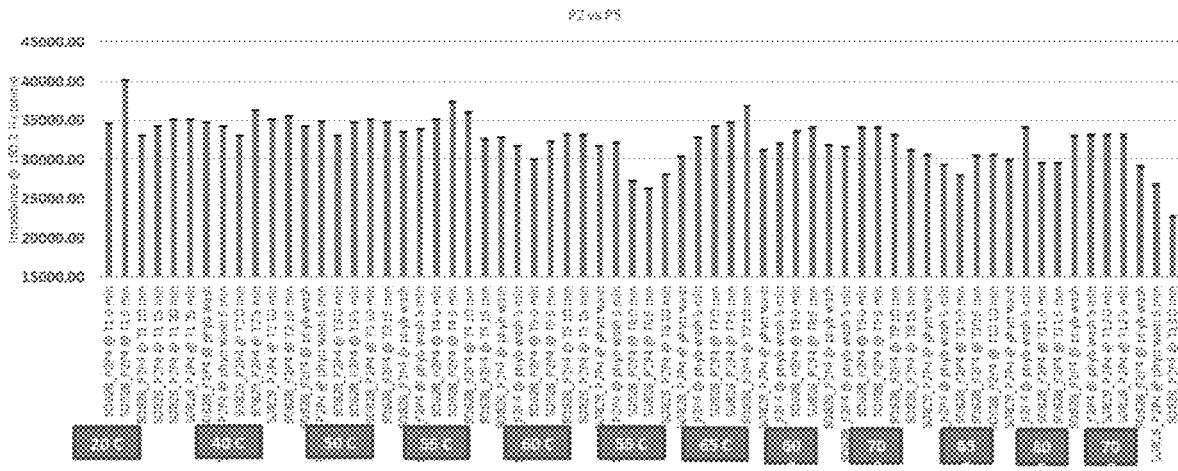
FIG. 18 A graph of estimated impedance regarding interaction of non-specific miRNA sequence with capture probe (P2) at various temperatures and times.

An estimation of signal for interaction of non-specific miRNA sequence with capture probe (P2) is shown in FIG. 18.

Figure 19:
FIG. 19 A graph of estimated impedance regarding the interaction of salmon sperm DNA with capture probe (P2) at various temperatures and times.

FIG. 19 illustrates an estimation of signal for interaction of salmon sperm DNA with capture probe (P2).

REFERENCES

The following references, to the extent that they provide exemplary procedural or other details supplementary to those set forth herein, are specifically incorporated herein by reference.

Reighard & Barendt, "Conformal Coating Process Controls: The Manufacturing Engineer's Aid." *APEX*. Long Beach, Calif. March 2000.

Vestergaard, et al., *Sensors*. 7(12):3442-58, 2007.

What is claimed is:

1. A handheld device for measuring a target analyte comprising:
   (a) a programmable gain amplifier configured to be operably coupled to a first electrode, a second electrode, and a third electrode; and
   (b) a programmable microcontroller operably coupled to the programmable gain amplifier, the first electrode, the second electrode, and the third electrode;
   wherein the programmable microcontroller is operable to apply a first alternating input electric voltage between the first electrode and the second electrode; the programmable microcontroller is operable to apply a second alternating input electric voltage between the third electrode and the second electrode; the programmable gain amplifier is operable to amplify an alternating output current flowing from the first electrode and from the third electrode through the second electrode;
   the programmable microcontroller is operable to calculate an impedance by comparing the first input electric voltage and the second input electric voltage to the measured output current; the programmable microcontroller is operable to calculate a target analyte concentration from the calculated impedance; and, the programmable microcontroller is operable to use multi-slice splitting and signal analysis to determine a frequency at which the impedance change is at a maximum or minimum.

2. The handheld measuring device of claim 1, wherein the programmable microcontroller is operable to apply the first alternating input electric voltage and the second alternating input electric voltage that have a frequency between 50 Hz and 1,000 Hz.

3. The handheld measuring device of claim 1, wherein the programmable microcontroller is operable to apply the first alternating input electric voltage and the second alternating input electric voltage that are sinusoidal.

4. The handheld measuring device of claim 1, wherein the programmable microcontroller is operable to apply the first alternating input electric voltage and the second alternating input electric voltage that are sawtooth waves.

5. The handheld measuring device of claim 1, wherein the programmable microcontroller is operable to apply the first alternating input electric voltage and the second alternating input electric voltage that are square waves.

6. The handheld measuring device of claim 1, wherein the programmable gain amplifier has a variable gain of between 1 and 200.

7. The handheld measuring device of claim 1, wherein the microcontroller is operable to apply a first alternating input electric voltage and a second alternating input electric voltage of between 5 mV and 500 mV.

8. The handheld measuring device of claim 1, wherein the handheld measuring device is operable to detect an output current of 10 pA or greater.

9. The handheld measuring device of claim 1, wherein the programmable microcontroller comprises an analog to digital converter and a digital to analog converter.

10. The handheld measuring device of claim 1, wherein the programmable microcontroller is operable to apply a fast Fourier transform to the input electric voltage and output current to calculate impedance as a function of frequency.

11. The handheld measuring device of claim 1, wherein the programmable microcontroller is operable to apply a Laplace transform to the input electric voltage and output current to calculate impedance as a function of frequency.

12. The handheld measuring device of claim 1, further comprising a liquid crystal display operably coupled to the programmable microcontroller; a mini joystick operably coupled to the programmable microcontroller; wherein the mini joystick is operable to allow users to provide input; and the liquid crystal display is capable of displaying output data.

13. The handheld measuring device of claim 1, further comprising a smartphone operably coupled to the programmable microcontroller; wherein the smartphone is operable to allow users to provide input; and the smartphone is capable of displaying output data.

14. The handheld measuring device of claim 1, wherein the output data comprises the target analyte concentration.

15. The handheld measuring device of claim 1, wherein the output data comprises the impedance.

16. The handheld measuring device of claim 1, wherein the handheld measuring device does not contain a redox probe.

17. A handheld device for measuring a target analyte comprising:
  (a) a programmable gain amplifier configured to be operably coupled to a first electrode, a second electrode, and a third electrode;
  (b) a programmable microcontroller operably coupled to the programmable gain amplifier, the first electrode, the second electrode, and the third electrode;
wherein the programmable microcontroller is operable to apply a first alternating input electric voltage between the first electrode and the second electrode; the programmable microcontroller is operable to apply a second alternating input electric voltage between the third electrode and the second electrode; the programmable gain amplifier is operable to shift the angular orientation of an electric field of the second alternating input electric voltage; the programmable gain amplifier is operable to amplify an alternating output current flowing through the third electrode; the programmable microcontroller is operable to calculate an amplitude of the alternating output current; the programmable microcontroller is operable to detect a presence of one or more target analytes by comparing the angular orientation to the amplitude of the alternating output current and, the programmable microcontroller is operable to use multi-slice splitting and signal analysis to determine a frequency at which the impedance change is at a maximum or minimum.

18. The handheld measuring device of claim 17, wherein the programmable microcontroller is operable to shift the angular orientation from 0 to 360 degrees.

* * * * *